United States Patent [19]

Hartley

[11] Patent Number: 5,449,758

[45] Date of Patent: Sep. 12, 1995

[54] PROTEIN SIZE MARKER LADDER

[75] Inventor: James L. Hartley, Frederick, Md.

[73] Assignee: Life Technologies, Inc., Gaithersburg, Md.

[21] Appl. No.: 160,670

[22] Filed: Dec. 2, 1993

[51] Int. Cl.⁶ .................... C07K 14/00; C12P 21/00; C12P 21/02; C12P 21/06

[52] U.S. Cl. .................... 530/350; 435/68.1; 435/69.1; 435/69.7; 435/810

[58] Field of Search .......... 530/350; 935/47; 435/69.7, 870, 68.1, 69.1

[56] References Cited

U.S. PATENT DOCUMENTS

| | | | |
|---|---|---|---|
| 4,403,036 | 9/1983 | Hartley et al. | 435/320.1 |
| 4,569,794 | 2/1986 | Smith et al. | 530/344 |
| 5,030,566 | 7/1991 | Son et al. | 435/91 |
| 5,284,762 | 2/1994 | Hayano et al. | 435/233 |

OTHER PUBLICATIONS

Anderson et al., J. Biol. Chem. 254:939–944 (1979).
Nefsky et al., Proc. Natl. Acad. Sci. USA 86:3549–3553 (1989).
Mazzorana et al., J. Biol. Chem. 268: 3029–3032 (1993).
Gearing, D. P. et al., Production of Leukemia Inhibitory Factor in *Escherichia coli* by a Novel Procedure and its Use In Maintaining Embryonic Stem Cells in Culture, *Bio/Technology* 7:1157–1161 (Nov. 1989).
Germino, J. et al., Rapid purification of a cloned gene product by genetic fusion and site–specific proteolysis, *Proc. Natl. Acad. Sci.* USA 81:4692–4696 (Aug. 1984).
Giedroc, D. P. et al., Overexpression, Purification, and Characterization of Recombinant T4 Gene 32 Protein₂₋₂₋₃₀₁ (G32P-B), *J. Biol. Chem.* 265 (20):11444–11455 (Jul. 15, 1990).
Gross, E., The Cyanogen Bromide Reaction, Methods in Enzymology 11:238–255 (1966).
Haffey, M. L. et al., Site–Specific Cleavage of a Fusion Protein by Renin, *DNA* 6(6):565–571 (1987).
Hartley, J. L. et al., Cloning multiple copies of a DNA segment, *Gene* 13:347–353 (1981).
Itakura, K. et al., Expression in *Escherichia coli* of a Chemically Synthesized Gene for the Hormone Somatostatin, *Science* 198:1056–1063 (Dec. 9, 1977).
Life Technologies, 1993–1994 *Catalogue and Reference Guide*, pp. 8–16-8–20.
Nagai, K. et al., Synthesis and Sequence–Specific Proteolysis of Hybrid Proteins Produced in *Escherichia coli*, *Methods in Enzymology* 153:461–481 (1987).
Pharmacia Biotech Inc., *Molecular and Cell Biology Catalog* 1993, p. 78.
Shen, S., Multiple joined genes prevent product degradation in *Escherichia coli*, *Proc. Natl. Acad. Sci. USA* 81:4627–4631 (Aug. 1984).
Szoka, P. R. et al., A General Method for Retrieving the Components of a Genetically Engineered Fusion Protein, *DNA* 5(1):11–20 (1986).
Villa, S. et al., Expression in *Escherichia coli* and Characterization of human growth–hormone–releasing factor, *Eur. J. Biochem.* 171:137–141 (1988).

*Primary Examiner*—Keith C. Furman
*Assistant Examiner*—Eric Grimes
*Attorney, Agent, or Firm*—Sterne, Kessler, Goldstein & Fox

[57] ABSTRACT

The invention relates to a multidomain protein comprising sites for cleavage of the protein into at least 3 polypeptide domains; nucleic acid encoding the multidomain protein; a protein ladder comprising a collection of protein fragments obtained by the partial cleavage of one or more multidomain proteins by one or more cleaving agents; and methods of using and preparing the protein ladder.

12 Claims, 1 Drawing Sheet

PROTEIN SIZE MARKER LADDER

BACKGROUND OF THE INVENTION

Field of the Invention

The present invention is in the field of molecular biology and specifically relates to the technique of gel electrophoresis of proteins.

Background Information

Gel electrophoresis of proteins is a well known technique in molecular biology which separates proteins on the basis of their size (See *Current Protocols in Molecular Biology*, Eds. Ausubel et al., *Current Protocols*, U.S.A., Vol. 2, pp. 10.2.1–10.2.21 (1993)).

A number of mixtures of proteins are commercially available that can be used as markers for determining or estimating the sizes of proteins during gel electrophoresis. For example, the protein molecular weight standard, Life Technologies, 1993–1994 catalogue, Cat. No. 16001–018 is composed of seven proteins: myosin (H-chain; 200,000 Da), phosphorylase b (97,400 Da), bovine serum albumin (68,000), ovalbumin (43,000 Da), carbonic anhydrase (29,000 Da), B-lactoglobulin (18,400 Da) and lysozyme (14,300).

SUMMARY OF THE INVENTION

In general, the present invention provides a protein ladder. More specifically, the present invention provides a protein ladder comprising a collection of protein fragments obtained by the partial cleavage of one or more multidomain proteins by one or more cleaving agents wherein;

(a) the protein ladder contains at least 3 polypeptide fragments of different size;

(b) the multidomain protein comprises at least 3 polypeptide domains; and (c) the size of each of the fragments in kilodaltons is an integral multiple of the size of the domain.

The present invention also provides a multidomain protein comprising sites for cleavage of the protein into at least 3 polypeptide domains of the same size, wherein the size of the domain in kilodaltons is a multiple of an integer.

The present invention further provides a nucleic acid encoding the above-described multidomain protein.

The present invention also provides a protein marker kit comprising a carrier means having in close confinement therein at least one container means where the first container means contains the above-described protein ladder.

The present invention further provides a method of using a protein ladder to estimate the size of a sample protein comprising:

(a) electrophoresing simultaneously in separate lanes of a gel the protein ladder above-described and the sample protein; and (b) comparing the size of fragments of said protein ladder with the size of the sample protein.

The present invention also provides a method of preparing a protein ladder comprising:

(a) inserting one or more DNA fragments comprising 5' and 3' asymmetric restriction site ends and a DNA sequence encoding a polypeptide domain comprising an amino-terminal subunit Y and a carboxy-terminal subunit Z into an asymmetric restriction site within a DNA vector, wherein the site separates a polypeptide domain comprising an amino-terminal subunit A from a carboxy-terminal subunit B, wherein a DNA sequence is produced which encodes a multidomain protein consisting essentially of at least 3 polypeptide domains of the same size, wherein one domain consists essentially of subunit A and subunit Y, one or more domains consist essentially of subunit Y and subunit Z, and one domain consists essentially of subunit Z and subunit B;

(b) expressing the multidomain protein in a cell;

(c) purifying the multidomain protein; and (d) partially cleaving the multidomain protein with a cleaving agent, wherein a protein ladder is produced wherein the ladder contains at least 3 fragments.

Further objects and advantages of the present invention will be clear from the description that follows.

DETAILED DESCRIPTION OF THE INVENTION

Figure 1:
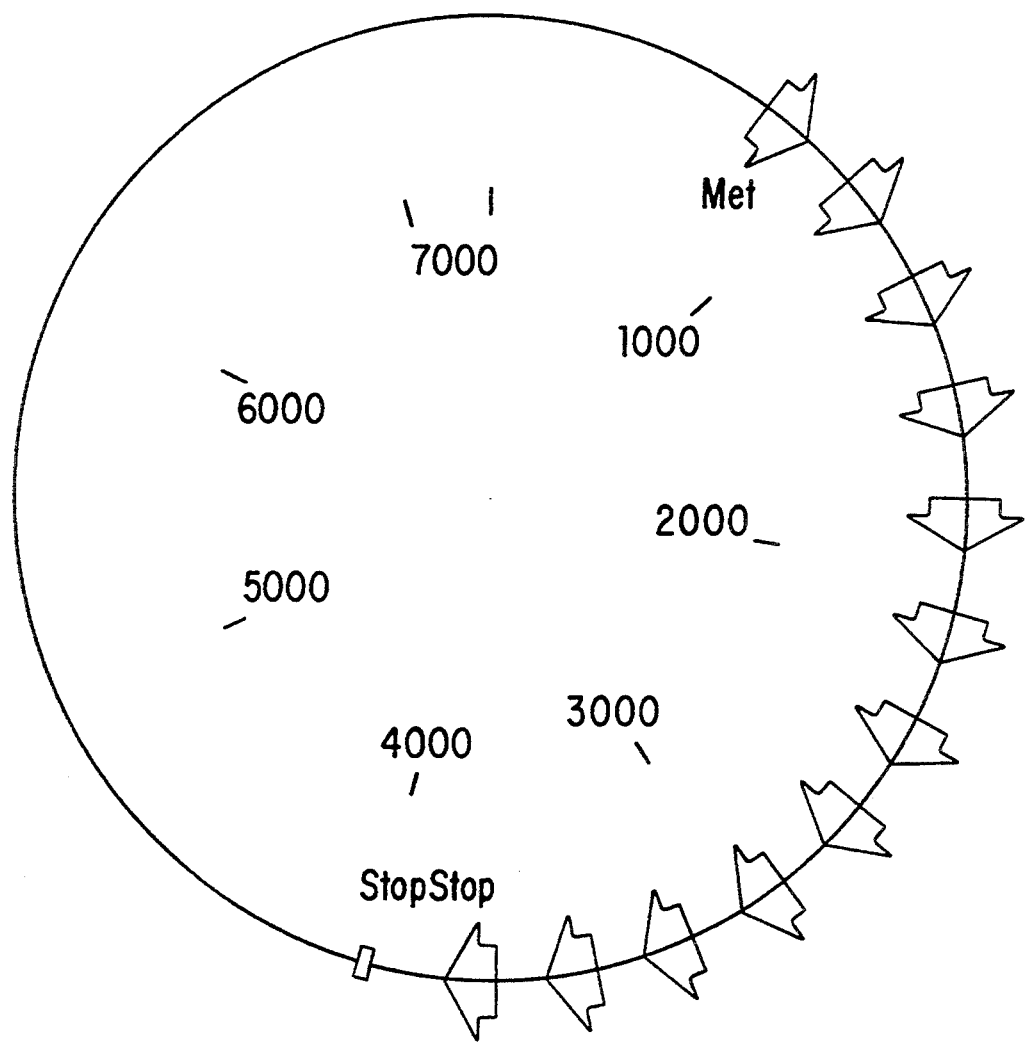
FIG. 1. A plasmid map of pPrL 3925 which contains a 12 mer clone in pTrc99A (Pharmacia).

The present invention relates to a protein ladder.

In one embodiment, the present invention relates to a protein ladder comprising:

a collection of protein fragments obtained by the partial cleavage of one or more multidomain proteins by one or more cleaving agents wherein;

(a) the protein ladder contains at least 3 polypeptide fragments of different size;

(b) the multidomain protein comprises at least 3 polypeptide domains; and (c) the size of each of the fragments in kilodaltons is an integral multiple of the size of the domain. In a preferred embodiment, the cleaving agent is cyanogen bromide (Itakura et al., *Science* 198:1053–1056 (1977); Szoka et al., *DNA* 5:11–20 (1986)). Cyanogen bromide cleaves after a methionine residue, resulting in fragments with carboxy terminal homoserines and amino terminal X, where X is the amino acid after methionine (E. Gross, *Methods in Enz.* 11:238–255, 1966). In another preferred embodiment, the cleaving agent is iodosobenzoic acid which cleaves by oxidation at tryptophan residues (Villa et al., *Eur. J. Biochem* 171:137–141 (1988)). In another preferred embodiment, the cleaving agent is a protease such as thrombin (which cleaves -Leu-Val-Pro-Arg- ↓ -Gly-Ser-Pro- (SEQ ID NO: 1)) (Gearing et al., *BioTechnology* 7:1157–1161 (1989)), factor Xa (which cleaves the tetrapeptide Ile-Glu-Gly-Arg (SEQ ID NO: 2)) (Nagai and Thogersen, *Methods Enzymol.* 153:461–481 (1987)), renin (which cleaves -Pro-Phe-His-Leu- ↓ -Leu-Val-Tyr- (SEQ ID NO: 3)) (Haffey et al., *DNA* 6:565–571 (1987)), collagenase (which cleaves -Pro-XXX- ↓ -Gly- (SEQ ID NO: 4)) (Germino and Bastia, *Proc. Natl. Acad. Sci. U.S.A.* 81:4692–4696 (1984)), trypsin, chymotrypsin, or papain.

In another preferred embodiment, the multidomain protein comprises at least 5 polypeptide domains. In a further preferred embodiment, the multidomain protein comprises at least 10 polypeptide domains.

In another embodiment, the present invention relates to a multidomain protein comprising sites for cleavage of the protein into at least 3 polypeptide domains of the same (preferably, identical) size wherein the size of the domain in kilodaltons is a multiple of an integer. Preferably, the integer is 5, 10, 15, 20, or 30. In one preferred embodiment, the cleaving site is methionine. In another preferred embodiment, the cleaving site is a recognition site for a protease as set forth above.

In a further embodiment, the present invention relates to a nucleic acid encoding the above-described multidomain protein.

In another embodiment, the present invention relates to a protein marker kit comprising a carrier means having in close confinement therein at least one container means such as a vial, tube or the like, where the first container means contains the above-described protein ladder.

In a further embodiment, the present invention relates to a method of using a protein ladder to estimate the size of a sample protein comprising:

(a) electrophoresing simultaneously on a gel the above-described protein ladder and the sample protein; and
(b) comparing the size of fragments of the protein ladder with the size of the sample protein.

In another embodiment, the present invention relates to a method of preparing a protein ladder comprising:

(a) inserting two or more DNA fragments comprising 5' and 3' asymmetric restriction site ends and a DNA sequence encoding a polypeptide domain comprising an amino-terminal subunit Y and a carboxy-terminal subunit Z into an asymmetric restriction site within a DNA vector, wherein the site separates a polypeptide domain comprising an amino-terminal subunit A from a carboxy-terminal subunit B, wherein a DNA sequence is produced which encodes a multidomain protein consisting essentially of at least 3 polypeptide domains of the same size, wherein one domain consists essentially of subunit A and subunit Y, one or more domains consist essentially of subunit Y and subunit Z, and one domain consists essentially of subunit Z and subunit B;
(b) expressing the multidomain protein in a cell;
(c) purifying the multidomain protein; and
(d) partially cleaving the multidomain protein with a cleaving agent, wherein a protein ladder is produced wherein the ladder contains at least 3 fragments.

For example, a multidomain protein with four domains would comprise the following structure:

<u>A Y Z Y Z Y Z B</u> wherein AY is one domain, ZB is another domain and the domain ZY is duplicated. The cleavage site is between the Y and the Z domains such that AY, ZB, and ZY are the same size. Although the domains ideally have about the same or identical molecular weights, the domains do not necessarily have to have the same sequence or even comprise the same amino acids.

The above-described multidomain protein can be created by inserting a nucleic acid fragment encoding YZ into a nucleic acid fragment encoding AB. Techniques for joining nucleic acids are well known in the art (See *Current Protocols in Molecular Biology*, Eds. Ausubel et al., Current *Protocols*, U.S.A. (1993) and Stunbrook et al., *Molecular Cloning, A Laboratory Manual*, second edition, Cold Spring Harbor Laboratory Press (1989) for general molecular biology techniques). Techniques for cloning tandem direct repeats of DNA segments have been described (Hartley and Gregori, *Gene* 13:347–353 (1981); Hartley and Gregori, U.S. Pat. No. 4,403,036). The number of domains present in the multidomain protein depends upon the number of nucleic acid fragments encoding YZ inserted into the nucleic acid fragment encoding AB.

In one preferred embodiment, the domains comprise the same amino acid sequence. In another preferred embodiment, the domains comprise the following amino acid sequence (SEQ ID NO: 4):

```
Met Gly Phe Ser Ser Glu Asp Lys Gly Glu Trp Lys Leu Lys Leu
Asp Asn Ala Gly Asn Gly Gln Ala Val Ile Arg Phe Leu Pro Ser
Lys Asn Asp Glu Gln Ala Pro Phe Ala Ile Leu Val Asn His Gly
Phe Lys Lys Asn Gly Lys Trp Tyr Ile Glu Thr Ser Ser Thr His
Asp Tyr Asp Ser Pro Val Gln Tyr Ile Ser Lys Asn Asp Leu Gly
Tyr Asn Thr Asp Asn Lys Glu Tyr Val Leu Val Lys Leu
```

In another preferred embodiment, a multidomain protein comprising 6 domains is constructed by inserting four Ava I fragments, each encoding a permuted domain (domain YZ rearranged such that AY is equivalent in size to ZB), into an Ava I site within a nonpermuted domain (AB) which results in the following sequence (SEQ ID NO: 5):

```
Met Gly Phe Ser Ser Glu Asp Lys Gly Glu Trp Lys Leu Lys Leu
Asp Asn Ala Gly Asn Gly Gln Ala Val Ile Arg Phe Leu Pro Ser
Lys Asn Asp Glu Gln Ala Pro Phe Ala Ile Leu Val Asn His Gly
Phe Lys Lys Asn Gly Lys Trp Tyr Ile Glu Thr Ser Ser Thr His
Asp Tyr Asp Ser Pro Val Gln Tyr Ile Ser Lys Asn Asp Leu Gly
Tyr Asn Thr Asp Asn Lys Glu Tyr Val Leu Val Lys Leu
(Met Gly Phe Ser Ser Glu Asp Lys Gly Glu Trp Lys Leu Lys Leu
Asp Asn Ala Gly Asn Gly Gln Ala Val Ile Arg Phe Leu Pro Ser
Lys Asn Asp Glu Gln Ala Pro Phe Ala Ile Leu Val Asn His Gly
Phe Lys Lys Asn Gly Lys Trp Tyr Ile Glu Thr Ser Ser Thr His
Asp Tyr Asp Ser Pro Val Gln Tyr Ile Ser Lys Asn Asp Leu Gly
Tyr Asn Thr Asp Asn Lys Glu Tyr Val Leu Val Lys Leu)4
```

-continued

```
Met Gly Phe Ser Ser Glu Asp Lys Gly Glu Trp Lys Leu Lys Leu
Asp Asn Ala Gly Asn Gly Gln Ala Val Ile Arg Phe Leu Pro Ser
Lys Asn Asp Glu Gln Ala Pro Phe Ala Ile Leu Val Asn His Gly
Phe Lys Lys Asn Gly Lys Trp Tyr Ile Glu Thr Ser Ser Thr His
Asp Tyr Asp Ser Pro Val Gln Tyr Ile Ser Lys Asn Asp Leu Gly
Tyr Asn Thr Asp Asn Lys Glu Tyr Val Leu Val Lys Leu
```

In another preferred embodiment, at least one domain contains neighboring histidines. The presence of neighboring histidines in the domain enables the protein to be purified over a nickel column (Smith et al., U.S. Pat. No. 4,569,794). In a further preferred embodiment, at least one domain contains six neighboring histidines. Ideally, the neighboring histidine group comprises His-His-His-His-His-His (SEQ ID NO: 6). The neighboring histidine group may be placed anywhere in the sequence of the domain. In one preferred embodiment, the neighboring histidine group is placed at either the amino-terminus or the carboxy-terminus In another preferred embodiment, the neighboring histidine group is present only in the carboxy-terminal domain of the multidomain protein. In a further preferred embodiment, the neighboring histidine group is present in all of the domains of the multidomain protein. In another preferred embodiment, at least one domain comprises the following amino acid sequence (SEQ ID NO: 7):

```
Met Gly Phe Ser Ser Glu Asp Lys Gly Glu Trp Lys Leu Lys Leu
Asp Asn Ala Gly Asn Gly Gln Ala Val Ile Arg Phe Leu Pro Ser
Lys Asn Asp Glu Gln Ala Pro Phe Ala Ile Leu Val Asn His Gly
Phe Lys Lys Asn Gly Lys Trp Tyr Ile Glu Thr Ser Ser Thr His
Asp Tyr Asp Ser Pro Val Gln Tyr Ile Ser Lys Asn Asp Leu Gly
Tyr Asn Thr Asp Asn Lys His His His His His His
```

In a further preferred embodiment, a six domain multidomain protein comprises the following amino acid sequence (SEQ ID NO: 8):

```
 Met Gly Phe Ser Ser Glu Asp Lys Gly Glu Trp Lys Leu Lys Leu
 Asp Asn Ala Gly Asn Gly Gln Ala Val Ile Arg Phe Leu Pro Ser
 Lys Asn Asp Glu Gln Ala Pro Phe Ala Ile Leu Val Asn His Gly
 Phe Lys Lys Asn Gly Lys Trp Tyr Ile Glu Thr Ser Ser Thr His
 Asp Tyr Asp Ser Pro Val Gln Tyr Ile Ser Lys Asn Asp Leu Gly
 Tyr Asn Thr Asp Asn Lys Glu Tyr Val Leu Val Lys Leu
(Met Gly Phe Ser Ser Glu Asp Lys Gly Glu Trp Lys Leu Lys Leu
 Asp Asn Ala Gly Asn Gly Gln Ala Val Ile Arg Phe Leu Pro Ser
 Lys Asn Asp Glu Gln Ala Pro Phe Ala Ile Leu Val Asn His Gly
 Phe Lys Lys Asn Gly Lys Trp Tyr Ile Glu Thr Ser Ser Thr His
 Asp Tyr Asp Ser Pro Val Gln Tyr Ile Ser Lys Asn Asp Leu Gly
 Tyr Asn Thr Asp Asn Lys Glu Tyr Val Leu Val Lys Leu)$_4$
 Met Gly Phe Ser Ser Glu Asp Lys Gly Glu Trp Lys Leu Lys Leu
 Asp Asn Ala Gly Asn Gly Gln Ala Val Ile Arg Phe Leu Pro Ser
 Lys Asn Asp Glu Gln Ala Pro Phe Ala Ile Leu Val Asn His Gly
 Phe Lys Lys Asn Gly Lys Trp Tyr Ile Glu Thr Ser Ser Thr His
 Asp Tyr Asp Ser Pro Val Gln Tyr Ile Ser Lys Asn Asp Leu Gly
 Tyr Asn Thr Asp Asn Lys His His His His His His
```

The multidomain protein described immediately above is an example of a multidomain protein which comprises different amino- and carboxy-terminal domains.

In a further preferred embodiment, a three domain multidomain protein comprises the following amino acid sequence (SEQ ID NO: 45):

```
Met Ala His His His His His His Pro His Val Lys Val Gly Asn
Leu His Ile Phe Gly Arg His Gly Glu Gly Tyr Ser Gly Pro Ser
Tyr Thr Asp Ala Asn His Lys His Leu Asn Trp Asp Glu Asn Asn
Lys Ser Glu Tyr Leu Thr Asn Pro Lys Tyr Lys Ile Pro Gly Lys
Thr Lys Gly Lys Ala Phe Gly Gly Lys Leu Lys Glu Asp Lys Arg
Asn Asp Leu Ile Thr Tyr Leu Lys Ala Lys Cys Glu Met Ala His
His His His His Pro His Val Lys Val Gly Asn Leu His Ile
Phe Gly Arg His Gly Glu Gly Tyr Ser Gly Pro Ser Tyr Thr Asp
Ala Asn His Lys His Leu Asn Trp Asp Glu Asn Asn Lys Ser Glu
Tyr Leu Thr Asn Pro Lys Tyr Lys Ile Pro Gly Lys Thr Lys Gly
Lys Ala Phe Gly Gly Lys Leu Lys Glu Asp Lys Arg Asn Asp Leu
Ile Thr Tyr Leu Lys Ala Lys Cys Glu Met Ala His His His His
His His Pro His Val Lys Val Gly Asn Leu His Ile Phe Gly Arg
His Gly Glu Gly Tyr Ser Gly Pro Ser Tyr Thr Asp Ala Asn His
Lys His Leu Asn Trp Asp Glu Asn Asn Lys Ser Glu Tyr Leu Thr
Asn Pro Lys Tyr Lys Ile Pro Gly Lys Thr Lys Gly Lys Ala Phe
Gly Gly Lys Leu Lys Glu Asp Lys Arg Asn Asp Leu Ile Thr Tyr
Leu Lys Ala Lys Cys Glu
```

The multidomain proteins are cleaved with the cleaving agent. One preferred cleaving agent is cyanogen bromide. The conditions of used for cleaving a protein with cyanogen bromide are well known in the art (Itakura et al., *Science* 198:1056–1053 (1977); Szoka et al., *DNA* 5:11–20 (1986)).

In a further embodiment, the present invention relates to a protein ladder that has been derivatized by the addition of dye molecules, whether visible or fluorescent, isotopic labels such as $^{14}C$, or other reporter groups such as biotin, digoxigefin, sugars, or antigens. These derivatives are useful in applications where it is desirable to detect the protein ladder by means other than traditional protein stains such as Coomassie blue.

The present invention is described in further detail in the following non-limiting examples.

EXAMPLE 1

A 10 Kd Protein Ladder

A gene encoding a multidomain protein, wherein each domain is 9,999 daltons (calculated molecular weight of 12 mer=119,983) was constructed. Each domain was designed to start with a methionine. Therefore, when the purified protein was reacted with cyanogen bromide at acidic pH, cleavage at the methionines occurred. Partial cleavage is desired, to yield ladder bands from 10 kd up to the size of the intact protein.

The gene encoding the multidomain protein consists of multiple repeats of 264 bp, arranged in a head-to-tail fashion. The monomeric subunit was modeled from a part of the bacteriophage T4 gene 32 protein (GenBank release 63.0, record #8457; D. P. Giedrox et al., *J. Biol. Chem.* 265:11444 (1990)).

The first 21 amino acid coding region of the bacteriophage T4 gene 32 protein was deleted. Additionally, the sequence coding for amino acids 22–110 of the bacteriophage T4 gene 32 protein was changed as follows:

a. an amino terminal methionine (atg) and a carboxy terminal leucine (ctt) were added;
b. amino acids 77 (Cys), 82 (Gly), 87 (Cys), and 90 (Cys) were deleted;
c. the Leu codon 98 was changed from cta to ctc, and the bases ggg (Gly) were inserted between 98 and 99 to make an asymmetric Ava I site (ctcggg); and
d. codon 107 was changed from agt (Ser) to git (Val).

The DNA sequence encoding the monomer was assembled in vitro from synthetic oligonucleotides as follows:

Scheme for the unpermuted gene:

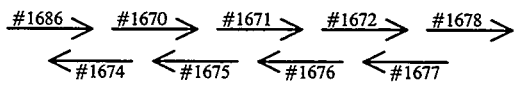

Scheme for the permuted gene:

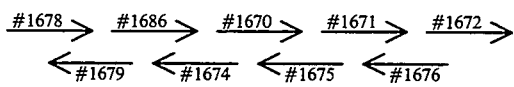

There were five coding strand oligos used for both the permuted and for the unpermuted gene:

1686: atg ggt ttt tct tct gaa gat aaa ggc gag tgg aaa ctg aaa ctc gat aat gcg gg (56mer)   (SEQ ID NO: 9)

1670: taa cgg tca agc agt aat tcg ttt tct tcc gtc taa aaa tga tga aca agc acc a (55mer)   (SEQ ID NO: 10)

1671: ttc gca att ctt gta aat cac ggt ttc aag aaa aat ggt aaa tgg tat att gaa a (55mer)   (SEQ ID NO: 11)

1672: cat cat cta ccc atg att acg att ctc cag tac aat aca tca gta aaa atg at (53mer)   (SEQ ID NO: 12)

1678: ctc ggg tac aac act gac aat aaa gag tac gtt ctt gtt aaa ctt (45mer)   (SEQ ID NO: 13)

There were four splice oligos for the unpermuted gene:

1674: act gct tga ccg tta ccc gca tta tcg agt (30mer)   (SEQ ID NO: 14)

1675: tac aag aat tgc gaa tgg tgc ttg ttc atc (30mer)   (SEQ ID NO: 15)

1676: cat ggg tag atg atg ttt caa tat acc att (30mer)   (SEQ ID NO: 16)

1677: agt gtt gta ccc gag atc att ttt act gat (30mer)   (SEQ ID NO: 17)

There was a different splice oligo for the permuted gene:

1679: aga aga aaa acc cat aag ttt aac aag aac (30mer)   (SEQ ID NO: 18)

The PCR primers for the unpermuted gene were:

1680: gau aua ucc aug ggt ttt tct tct gaa gat aaa g   (SEQ ID NO: 19)

1734: gau uac uua uua aag ttt aac aag aac gta ctc tt   (SEQ ID NO: 20)

The PCR primers for the permuted gene were:

1682: gau aua ucc aug ctc ggg tac aac act gac aa   (SEQ ID NO: 21)

1683: gau uac uua uua ccc gag atc att ttt act gat gta ttg tac   (SEQ ID NO: 22)

The unpermuted coding strand was assembled from gel purified oligos: oligos 1670, 1671, 1672, and 1678 were kinased. Three picomoles of each kinased oligo were mixed with 3 pmol of each unkinased oligos (the 5'-most oligo of the coding strand) and 1674, 1675, 1676, and 1677 (the four splice oligos). The coding strand oligo at the 3' end, #1678, was kinased with gamma =P-rATP. The mixture was incubated in kinase buffer (which also supports ligation with T4 DNA ligase) (50 mM Tris HCl pH 7.5, 10 mM $MgCl_2$, 5 mM DTT, 1 mM rATP, 50 µg/ml BSA) and ligated. Ligations were applied to a sequencing type gel, exposed to X-ray film, and a slice of gel containing the coding strand (5 oligos ligated together, total length 264 nt) was cut out and the DNA was eluted and purified.

A cloning vector was made for the PCR products as follows:

Two oligos were hybridized to make the "left arm":

1295: agc tag aaa taa ttt tgt tta act tta aga agg aga tat atc cat g   (SEQ ID NO: 23)

-continued

1296: tcc ttc tta aag tta aac aaa att att tct    (SEQ ID NO: 24)

Two oligos were hybridized to make the "right arm":

1297: aat tcc agg tcg act cta gag att act tat ta    (SEQ ID NO: 25)

1298: tct aga gtc gac ctg g    (SEQ ID NO: 26)

Oligos #1295 and #1297 were kinased with gamma =P-rATP. Oligo #1295 was hybridized to #1296 and Oligo #1297 was hybridized to #1298. Both hybrids (about 100 pmol each) were mixed with 2.5 μg (about 1 pmol) of pSP18 (3005 bp; LTI 1988 catalog, cat. #5361SA) cut with both HindIII and EcoRI, in a volume of about 100 μl, for one hour at room temperature with 32 units T4 ligase. The entire reaction was applied to a small Sephadex G-25 column, and the void volume fraction was collected. The resulting linear molecule had protruding 12 base 3' ends.

The purified 264 mer coding strand for the unpermuted gene was amplified via PCR with primer #1680 and primer #1734. One μl of PCR product was mixed with about 30 ng of the clog vector and one unit of uracil DNA glycosylase (UDG) in a total volume of 20 μl in PCR buffer. The mixture was incubated 37° for 45 minutes. The UDG removed the uracil bases from the PCR primers, creating 3' protruding ends which annealed to the 3' ends of the cloning vector (Berninger, U.S. Pat. No. 5,137,814). One μl was transformed into DH5α cells. Miniprep DNA was made from twelve colonies. Note that the stop codons were incorporated by incorporating their complementary sequence into primer #1734, and that the NcoI (C CATGG) site at the ATG start codon was incorporated by including the necessary bases into primer #1680. After sequencing candidate clones, a clone was found, called pPrL2201, that was perfect except for a mutation (the 52nd base of oligo #1670 changed from "a" to "c"). This did not change the amino acid sequence.

The stone procedure was used for assembling the permuted coding strand. Oligos 1672 (labelled with =p), 1671, 1670, 1686, and 1678 were ligated together, gel purified, and the purified 264 mer was amplified via PCR (primer #1682 and #1683). The two Ava I sims required for excising the permuted gene were present in the 5' end of oligo #1678, and in the PCR primer #1683, respectively. The PCR product was cloned into the modified pSP18 vector as above. Candidate clones were sequenced. The correct (i.e., no mutations) sequence was found in clone pPrL2107.

The 264 bp Ava I fragment containing the permuted gene was prepared from pPrL2107, and multiple copies of this were ligated into the Ava I site of clone pPrL2201 (above). This multimeric gene was found not to express efficiently in pSP18, so the multimeric gene was excised from pSP 18 by cutting with EcoRI, filled in to make blunt, cut with NcoI, and cloned into pTrc99a (Pharmacia) (that had been cut with SalI, filled in to make blunt, and cut with NcoI). The pTrc99A expression vector (Amann et al., (1988) *Gene* 69:301) contains a strong promoter (trc) upstream of the multiple cloning site and a strong transcription termination signal (rrnB) downstream. pTrc99A also contains the lac I$^q$ gene, the pBR322 ori and confers ampicillin resistance. Proteins expressed from this clone and derivatives (i.e. with various numbers of repeats) were found as inclusion bodies in *E. coli* DH10B cells following induction with IPTG.

To make the ladder, protein inclusion bodies from *E. coli* strain DH10B containing plasmid pPrL3925 (12 repeats) were purified by multiple cycles of sonication and centrifugation. The protein was dissolved 10 mM Tris HCl pH 7.5, 1 mM EDTA, 1% SDS, to a concentration of about 30 A280 units per ml. Three volumes of this were added to seven volumes of 100% formic acid (Sigma) and mixed until the protein was completely dissolved. Then cyanogen bromide (dissolved in formic acid; Aldrich) was added to a concentration of about 0.2 mg/ml. After overnight incubation in the dark at room temperature, the protein was precipitated by diluting the entire reaction into four volumes of water. The precipitate was collected by centrifugation, excess acid was removed with an alcohol wash, and the protein was dissolved in 50 mM Tris HCl pH 8.0, 1 mM EDTA, 1% SDS, 0.1% β-mercaptoethanol. SDS polyacrylimide gel electrophoresis analysis of protein ladders was perforated on precast 8 to 16 % gradient gels (Novex, San Diego, Calif.) according to the manufacturer's instructions, at a constant power of 5 watts per gel. The Dmds showed the expected electrophoretic mobilities, with no doublets. Other electrophoresis conditions may give different results.

The following is the sequence of a 3-mer (SEQ ID NOS: 27 AND 28), determined by DNA sequencing, containing the silent mutation in first domain only: multiple copies of permuted gene from plasmid pPrL2107 cloned into the unpermuted gene in pPrL2201.

```
atg ggt ttt tct tct gaa gat aaa ggc gag tgg aaa ctg aaa ctc   45
Met Gly Phe Ser Ser Glu Asp Lys Gly Glu Trp Lys Leu Lys Leu gat aat gcg ggt aac ggt caa gca gta att cgt ttt ctt ccg tct   90
Asp Asn Ala Gly Asn Gly Gln Ala Val Ile Arg Phe Leu Pro Ser aaa aat gat gaa caa gcc cca ttc gca att ctt gta aat cac ggt  135
Lys Asn Asp Glu Gln Ala Pro Phe Ala Ile Leu Val Asn His Gly ttc aag aaa aat ggt aaa tgg tat att gaa aca tca tct acc cat  180
Phe Lys Lys Asn Gly Lys Trp Tyr Ile Glu Thr Ser Ser Thr His gat tac gat tct cca gta caa tac atc agt aaa aat gat ctc ggg  225
Asp Tyr Asp Ser Pro Val Gln Tyr Ile Ser Lys Asn Asp Leu Gly tac aac act gac aat aaa gag tac gtt ctt gtt aaa ctt atg ggt  270
Tyr Asn Thr Asp Asn Lys Glu Tyr Val Leu Val Lys Leu Met Gly
```

-continued

| | | | | | | | | | | | | | | |
|---|---|---|---|---|---|---|---|---|---|---|---|---|---|---|
| ttt | tct | tct | gaa | gat | aaa | ggc | gag | tgg | aaa | ctg | aaa | ctc | gat | aat | 315
| Phe | Ser | Ser | Glu | Asp | Lys | Gly | Glu | Trp | Lys | Leu | Lys | Leu | Asp | Asn | gcg ggt aac ggt caa gca gta att cgt ttt ctt ccg tct aaa aat 360
Ala Gly Asn Gly Gln Ala Val Ile Arg Phe Leu Pro Ser Lys Asn gat gaa caa gca cca ttc gca att ctt gta aat cac ggt ttc aag 405
Asp Glu Gln Ala Pro Phe Ala Ile Leu Val Asn His Gly Phe Lys aaa aat ggt aaa tgg tat att gaa aca tca tct acc cat gat tac 450
Lys Asn Gly Lys Trp Tyr Ile Glu Thr Ser Ser Thr His Asp Tyr gat tct cca gta caa tac atc agt aaa aat gat ctc ggg tac aac 495
Asp Ser Pro Val Gln Tyr Ile Ser Lys Asn Asp Leu Gly Tyr Asn act gac aat aaa gag tac gtt ctt gtt aaa ctt atg ggt ttt tct 540
Thr Asp Asn Lys Glu Tyr Val Leu Val Lys Leu Met Gly Phe Ser tct gaa gat aaa ggc gag tgg aaa ctg aaa ctc gat aat gcg ggt 585
Ser Glu Asp Lys Gly Glu Trp Lys Leu Lys Leu Asp Asn Ala Gly aac ggt caa gca gta att cgt ttt ctt ccg tct aaa aat gat gaa 630
Asn Gly Gln Ala Val Ile Arg Phe Leu Pro Ser Lys Asn Asp Glu caa gca cca ttc gca att ctt gta aat cac ggt ttc aag aaa aat 675
Gln Ala Pro Phe Ala Ile Leu Val Asn His Gly Phe Lys Lys Asn ggt aaa tgg tat att gaa aca tca tct acc cat gat tac gat tct 720
Gly Lys Trp Tyr Ile Glu Thr Ser Ser Thr His Asp Tyr Asp Ser cca gta caa tac atc agt aaa aat gat ctc ggg tac aac act gac 765
Pro Val Gln Tyr Ile Ser Lys Asn Asp Leu Gly Tyr Asn Thr Asp aat aaa gag tac gtt ctt gtt aaa ctt 792
Asn Lys Glu Tyr Val Leu Val Lys Leu

EXAMPLE 2

A 10 Kd Protein Ladder With Six Histidines at the Carboxy-Terminus

A protein ladder was produced as described in Example 1, except for the substitution of 6 histidines in oligo #1673 in place of the final seven amino acids in oligo #1678.

Scheme for the unpermuted gene with His6:

1686 → #1670 → #1671 → #1672 → #1673 →
← #1674   ← #1675   ← #1676   ← #1677

Scheme for the permuted gene (no His6 because the permuted copies are internal, His6 at carboxy terminus):

1678 → #1686 → #1670 → #1671 → #1672 →
← #1679   ← #1674   ← #1675   ← #1676

There were five oligos encoding the unpermuted gene with carboxy terminal His6:

1686: atg ggt ttt tct tct gaa gat aaa ggc gag tgg aaa ctg aaa ctc gat aat gcg gg (56mer) (SEQ ID NO: 9)

1670: taa cgg tca agc agt aat tcg ttt tct tcc gtc taa aaa tga tga aca agc acc a (55mer) (SEQ ID NO: 10)

1671: ttc gca att ctt gta aat cac ggt ttc aag aaa aat ggt aaa tgg tat att gaa a (55mer) (SEQ ID NO: 11)

1672: cat cat cta ccc atg att acg att ctc cag tac aat aca tca gta aaa atg at (53mer) (SEQ ID NO: 12)

1673: ctc ggg tac aac act gac aat aaa cac cac cac cac cac cac (42mer) (SEQ ID NO: 29)

There were four splice oligos for the unpermuted gene:

1674: act gct tga ccg tta ccc gca tta tcg agt (30mer) (SEQ ID NO: 14)

1675: tac aag aat tgc gaa tgg tgc ttg ttc atc (30mer) (SEQ ID NO: 15)

1676: cat ggg tag atg atg ttt caa tat acc att (30mer) (SEQ ID NO: 16)

1677: agt gtt gta ccc gag atc att ttt act gat (30mer) (SEQ ID NO: 17)

There was a different splice oligo for the permuted gene:

1679: aga aga aaa acc cat agg ttt aac aag aac (30mer) (SEQ ID NO: 18)

There was a coding strand oligo for the permuted gene (no His6):

1678: ctc ggg tac aac act gac aat aaa gag tac gtt ctt gtt aaa ctt (45mer) (SEQ ID NO: 13)

PCR primers for the unpermuted gene with His6 were:

(SEQ ID NO: 19)

before the Ava I site, insertion of permuted copies of the gene into pPrL2001 results in a multidomain protein with the gly→ala change in the first domain but no others.

| atg | ggt | ttt | tct | tct | gaa | gat | aaa | ggc | gag | tgg | aaa | ctg | aaa | ctc | 45 |
| Met | Gly | Phe | Ser | Ser | Glu | Asp | Lys | Gly | Glu | Trp | Lys | Leu | Lys | Leu | |
| gat | aat | gcg | ggt | aac | ggt | caa | gca | gta | att | cgt | ttt | ctt | ccg | tct | 90 |
| Asp | Asn | Ala | Gly | Asn | Gly | Gln | Ala | Val | Ile | Arg | Phe | Leu | Pro | Ser | |
| aaa | aat | gat | gaa | caa | gca | cca | ttc | gca | att | ctt | gta | aat | cac | ggt | 135 |
| Lys | Asn | Asp | Glu | Gln | Ala | Pro | Phe | Ala | Ile | Leu | Val | Asn | His | Gly | |
| ttc | aag | aaa | aat | gct | aaa | tgg | tat | att | gaa | aca | tca | tct | acc | cat | 180 |
| Phe | Lys | Lys | Asn | Ala | Lys | Trp | Tyr | Ile | Glu | Thr | Ser | Ser | Thr | His | |
| gat | tac | gat | tct | cca | gta | caa | tac | atc | agt | aaa | aat | gat | ctc | ggg | 225 |
| Asp | Tyr | Asp | Ser | Pro | Val | Gln | Tyr | Ile | Ser | Lys | Asn | Asp | Leu | Gly | |
| tac | aac | act | gac | aat | aaa | gag | tac | gtt | ctt | gtt | aaa | ctt | atg | ggt | 270 |
| Tyr | Asn | Thr | Asp | Asn | Lys | Glu | Tyr | Val | Leu | Val | Lys | Leu | Met | Gly | |
| ttt | tct | tct | gaa | gat | aaa | ggc | gag | tgg | aaa | ctg | aaa | ctc | gat | aat | 315 |
| Phe | Ser | Ser | Glu | Asp | Lys | Gly | Glu | Trp | Lys | Leu | Lys | Leu | Asp | Asn | |
| gcg | ggt | aac | ggt | caa | gca | gta | att | cgt | ttt | ctt | ccg | tct | aaa | aat | 360 |
| Ala | Gly | Asn | Gly | Gln | Ala | Val | Ile | Arg | Phe | Leu | Pro | Ser | Lys | Asn | |
| gat | gaa | caa | gcc | cca | ttc | gca | att | ctt | gta | aat | cac | ggt | ttc | aag | 405 |
| Asp | Glu | Gln | Ala | Pro | Phe | Ala | Ile | Leu | Val | Asn | His | Gly | Phe | Lys | |
| aaa | aat | ggt | aaa | tgg | tat | att | gaa | aca | tca | tct | acc | cat | gat | tac | 450 |
| Lys | Asn | Gly | Lys | Trp | Tyr | Ile | Glu | Thr | Ser | Ser | Thr | His | Asp | Tyr | |
| gat | tct | cca | gta | caa | tac | atc | agt | aaa | aat | gat | ctc | ggg | tac | aac | 495 |
| Asp | Ser | Pro | Val | Gln | Tyr | Ile | Ser | Lys | Asn | Asp | Leu | Gly | Tyr | Asn | |
| act | gac | aat | aaa | gag | tac | gtt | ctt | gtt | aaa | ctt | atg | ggt | ttt | tct | 540 |
| Thr | Asp | Asn | Lys | Glu | Tyr | Val | Leu | Val | Lys | Leu | Met | Gly | Phe | Ser | |
| tct | gaa | gat | aaa | ggc | gag | tgg | aaa | ctg | aaa | ctc | gat | aat | gcg | ggt | 585 |
| Ser | Glu | Asp | Lys | Gly | Glu | Trp | Lys | Leu | Lys | Leu | Asp | Asn | Ala | Gly | |
| aac | ggt | caa | gca | gta | att | cgt | ttt | ctt | ccg | tct | aaa | aat | gat | gaa | 630 |
| Asn | Gly | Gln | Ala | Val | Ile | Arg | Phe | Leu | Pro | Ser | Lys | Asn | Asp | Glu | |
| caa | gcc | cca | ttc | gca | att | ctt | gta | aat | cac | ggt | ttc | aag | aaa | aat | 675 |
| Gln | Ala | Pro | Phe | Ala | Ile | Leu | Val | Asn | His | Gly | Phe | Lys | Lys | Asn | |
| ggt | aaa | tgg | tat | att | gaa | aca | tca | tct | acc | cat | gat | tac | gat | tct | 720 |
| Gly | Lys | Trp | Tyr | Ile | Glu | Thr | Ser | Ser | Thr | His | Asp | Tyr | Asp | Ser | |
| cca | gta | caa | tac | atc | agt | aaa | aat | gat | ctc | ggg | tac | aac | act | gac | 765 |
| Pro | Val | Gln | Tyr | Ile | Ser | Lys | Asn | Asp | Leu | Gly | Tyr | Asn | Thr | Asp | |
| aat | aaa | cac | cac | cac | cac | cac | cac | | | | | | | | 789 |
| Asn | Lys | His | His | His | His | His | His | | | | | | | | |

1680: gau aua ucc aug ggt ttt tct tct gaa gat aaa g (SEQ ID NO: 30)

1681: gau uac uua uua gtg gtg gtg gtg gtg gtg ttt

PCR primers for the permuted gene were:

(SEQ ID NO: 21)

1682: gau aua ucc aug ctc ggg tac aac act gac aa (SEQ ID NO: 22)

1683: gau uac uua uua ccc gag atc att ttt act gat gta ttg tac

A 3 mer clone with the six histidines at the carboxy terminus is shown below (SEQ ID NOS: 31 AND 32). Sequencing of clone pPrL2001: found a mutation in this sequence, the 38th base of oligo #1671 changed from g to c, changed the codon from ggt (gly) to gct (ala), an increase in MW of 14 daltons. Since this mutation is

EXAMPLE 3

A 10 Kd Protein Ladder with Six Histidines in Each Subunit

A protein ladder produced as described in Example 1, except as set forth below. This ladder was based on the yeast isocytochrome c gene (GenBmnk release 63.0, record #10068).

Cyanogen bromide partial cleavage of multidomain protein was done as described above. The ladder of bands so produced gave sharp bands, but smaller fragments appeared as doublets. The upper bands of these doublets could be removed by passage of the cleavage products over a nickel agarose column, demonstrating that fragments containing the carboxy-terminal histidines migrated more slowly upon electrophoresis than fragments lacking the six histidines.

Starting with the segment coord. 339-575:
1) An atg gct cac cac cac cac cac cac (SEQ ID NO: 49) (Met Ala His6) was added to the amino end.
2) Where possible, codons found in highly expressed *E. coli* proteins (P. Sharp et al., *Nucl. Acids Res.* 16:8207-8211 (1988)) were used.
3) An asymmetric Ava I site was created.
4) Two internal methionines were removed.
5) Other substitutions, deletions, and insertions to make molecular weight very close to 10,000 daltons as described below.

Scheme for assembly of unpermuted v.1 coding strand:

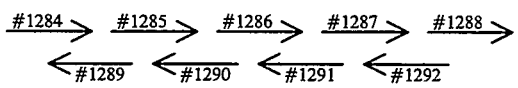

Scheme for assembly of permuted v. 1 coding strand:

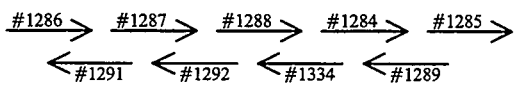

The coding strand oligos were:

1284: atg gct cac cac cac cac cac cac ccg cac gtt aaa gtt ggt aac (45mer)  (SEQ ID NO: 33)

1285: ctg cac atc ttc ggt cgt cac ggc gaa ggt tac agc gg (38mer)  (SEQ ID NO: 34)

1286: ccc gag cta cac cga cgc taa cca caa aca cct gaa ctg gga cga aaa caa caa aag cg (59mer)  (SEQ ID NO: 35)

1287: aat acc tga cca acc cga aat aca aaa ttc cgg gca aaa cca aag gta aag ctt tcg gt (59mer)  (SEQ ID NO: 36)

1288: ggc aaa ctg aaa gaa gac aaa cgt aac gac ctg atc acc tac ctg aaa gct aaa tgc gaa (60mer)  (SEQ ID NO: 37)

The splice oligos were:

1289: acc gaa gat gtg cag gtt acc aac ttt aac (30mer)  (SEQ ID NO: 38)

1290: tcg gtg tag ctc ggg ccg ctg taa cct tcg (30mer)  (SEQ ID NO: 39)

1291: ggt tgg tca ggt att cgc ttt tgt tgt ttt (30mer)  (SEQ ID NO: 40)

1292: ttc ttt cag ttt gcc acc gaa agc ttt acc (30mer)  (SEQ ID NO: 41)

The primers to amplify the unpermuted gene were:

1293: gau aua ucc aug gct cac cac cac cac (27mer)  (SEQ ID NO: 42)

1294: gau uac uua uua ttc gca ttt agc ttt cag gta (33mer)  (SEQ ID NO: 43)

Details of ligation, gel purification, PCR, cloning into pSP 18, and sequencing are the same as for Example 1.

Expression from plasmids containing multiple identical domains was done in *E. coli* strain BL21 containing a compatible plasmid, called pCP13-SP6 (RK2 replicon, derived from the cosmid vector pCP 13 (A. Darzins and A. M. Chakrabarty, *J. Bact.* 159:9-18 (1984))). pCP13-SP6 expressed SP6 RNA polymerase in a heat-inducible fashion. Shifting the temperature from 30° to 38° caused multimeric protein to be produced as inclusion bodies. After sonication, inclusion bodies were dissolved in 6M guanidine HCl, 0.1M $NaH_2PO_4$, 0.01M Tris base, 10 mM $\beta$-mercaptoethanol, pH 8.0 with NaOH, applied to a nickel agarose (DIAGEN GmbH, Hilden, Germany) column, washed with the stone buffer, washed with 8M urea, 0.1M $NaH_2PO_4$, 0.01M Tris base, pH 6.3 with HCl, 10 mM $\beta$-mercaptoethanol, and eluted with 8M urea, 0.1M $NaH_2PO_4$, 0.01 M Tris base, pH 4.5 with HCl, 10 mM $\beta$-mercaptoethanol. Following removal of the urea and other salts by dialysis, the purified protein was dissolved in 10 mM Tris HCl pH 7.5, 1% SDS, 20 mM $\beta$-mercaptoethanol. Cyanogen bromide partial cleavage was done as described above.

The ladder of bands showed no doublets, gave sharp bands, and stained well, except that the bands migrated somewhat anomalously. The fragments with an odd number of domains migrated more rapidly than expected, and/or the fragments with an even number of domains migrated more slowly than expected. Thus the 20 and 30 kd bands were a little too close together, the 30 and 40 kd bands were too far apart etc. This phenomenon was accentuated in lower percentage acrylimide gels, and could be abolished by including 8M urea in the gel. The following is the sequence of a 3-mer (SEQ ID NOS: 44 AND 45):

```
atg gct cac cac cac cac cac cac ccg cac gtt aaa gtt ggt aac    45
Met Ala His His His His His His Pro His Val Lys Val Gly Asn ctg cac atc ttc ggt cgt cac ggc gaa ggt tac agc ggc ccg agc    90
Leu His Ile Phe Gly Arg His Gly Glu Gly Tyr Ser Gly Pro Ser tac acc gac gct aac cac aaa cac ctg aac tgg gac gaa aac aac   135
Tyr Thr Asp Ala Asn His Lys His Leu Asn Trp Asp Glu Asn Asn aaa agc gaa tac ctg acc aac ccg aaa tac aaa att ccg ggc aaa   180
Lys Ser Glu Tyr Leu Thr Asn Pro Lys Tyr Lys Ile Pro Gly Lys acc aaa ggt aaa gct ttc ggt ggc aaa ctg aaa gaa gac aaa ctg   225
Thr Lys Gly Lys Ala Phe Gly Gly Lys Leu Lys Glu Asp Lys Arg aac gac ctg atc acc tac ctg aaa gct aaa tgc gaa atg gct cac   270
Asn Asp Leu Ile Thr Tyr Leu Lys Ala Lys Cys Glu Met Ala His
```

-continued

| | | | | | | | | | | | | | | |
|---|---|---|---|---|---|---|---|---|---|---|---|---|---|---|
| cac | cac | cac | cac | cac | ccg | cac | gtt | aaa | gtt | ggt | aac | ctg | cac | atc | 315
| His | His | His | His | His | Pro | His | Val | Lys | Val | Gly | Asn | Leu | His | Ile |

| ttc | ggt | cgt | cac | ggc | gaa | ggt | tac | agc | ggc | ccg | agc | tac | acc | gac | 360
| Phe | Gly | Arg | His | Gly | Glu | Gly | Tyr | Ser | Gly | Pro | Ser | Tyr | Thr | Asp |

| gct | aac | cac | aaa | cac | ctg | aac | tgg | gac | gaa | aac | aac | aaa | agc | gaa | 405
| Ala | Asn | His | Lys | His | Leu | Asn | Trp | Asp | Glu | Asn | Asn | Lys | Ser | Glu |

| tac | ctg | acc | aac | ccg | aaa | tac | aaa | att | ccg | ggc | aaa | acc | aaa | ggt | 450
| Tyr | Leu | Thr | Asn | Pro | Lys | Tyr | Lys | Ile | Pro | Gly | Lys | Thr | Lys | Gly |

| aaa | gct | ttc | ggt | ggc | aaa | ctg | aaa | gaa | gac | aaa | cgt | aac | gac | ctg | 495
| Lys | Ala | Phe | Gly | Gly | Lys | Leu | Lys | Glu | Asp | Lys | Arg | Asn | Asp | Leu |

| atc | acc | tac | ctg | aaa | gct | aaa | tgc | gaa | atg | gct | cac | cac | cac | cac | 540
| Ile | Thr | Tyr | Leu | Lys | Ala | Lys | Cys | Glu | Met | Ala | His | His | His | His |

| cac | cac | ccg | cac | gtt | aaa | gtt | ggt | aac | ctg | cac | atc | ttc | ggt | cgt | 585
| His | His | Pro | His | Val | Lys | Val | Gly | Asn | Leu | His | Ile | Phe | Gly | Arg |

| cac | ggc | gaa | ggt | tac | agc | ggc | ccg | agc | tac | acc | gac | gct | aac | cac | 630
| His | Gly | Glu | Gly | Tyr | Ser | Gly | Pro | Ser | Tyr | Thr | Asp | Ala | Asn | His |

| aaa | cac | ctg | aac | tgg | gac | gaa | aac | aac | aaa | agc | gaa | tac | ctg | acc | 675
| Lys | His | Leu | Asn | Trp | Asp | Glu | Asn | Asn | Lys | Ser | Glu | Tyr | Leu | Thr |

| aac | ccg | aaa | tac | aaa | att | ccg | ggc | aaa | acc | aaa | ggt | aaa | gct | ttc | 720
| Asn | Pro | Lys | Tyr | Lys | Ile | Pro | Gly | Lys | Thr | Lys | Gly | Lys | Ala | Phe |

| ggt | ggc | aaa | ctg | aaa | gaa | gac | aaa | cgt | aac | gac | ctg | atc | acc | tac | 765
| Gly | Gly | Lys | Leu | Lys | Glu | Asp | Lys | Arg | Asn | Asp | Leu | Ile | Thr | Tyr |

| ctg | aaa | gct | aaa | tgc | gaa | | | | | | | | | | 783
| Leu | Lys | Ala | Lys | Cys | Glu | | | | | | | | | |

EXAMPLE 4

A 10 Kd Protein Ladder with Methionine at Carboxy Terminal End

A gene encoding a multidomain protein, wherein each domain except the carboxy terminal is 10 kilodaltons, is constructed. Each domain is designed to start with a methionine. In addition, the carboxy terminal domain is identical to the other domains except that it contains one additional amino acid, methionine, as the final amino acid of the multidomain protein. Cleavage at the penultimate methionine releases a 10 kd fragment with the same number of amino acids as the internal 10 kd fragments, i.e. those fragments released by cyanogen bromide cleavage at adjacent methionines.

The gene encoding the multidomain protein consists of multiple repeats of 264 bp, with a final repeat of 267 bp, arranged in a head-to-tail fashion. The amino acid sequence is the stone as for example 1, above, with the single change of the addition of a carboxy terminal methionine.

The DNA sequence encoding the monomer is assembled in vitro from synthetic oligonucleotides as follows:

Scheme for assembly of the unpermuted gene:

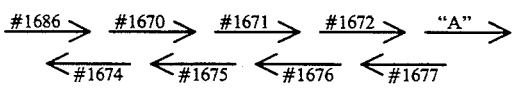

The Scheme For The Permuted Gene Is The Stone As In Example 1

The five oligos for the unpermuted gene are the stone as for example 1, except that oligo #1678 is replaced by oligo "A" (SEQ ID NO: 46):

"A": ctc ggg tac aac act gac aat aaa gag tca gtt ctt gtt aaa ctt atg (48mer)     (SEQ ID NO:46)

Oligos for the unpermuted gene, PCR primers, and splice oligos, are the same as for example 1, except that PCR primer #1734 is replaced by PCR primer "B":

(SEQ ID NO:47)
"B": gau uac uua uua cat aag ttt aac aag aac gta ctc tt (38mer)

The unpermuted coding strand is assembled from gel purified oligos 1686, 1670, 1671, 1672, and "A" and purified as in example 1. The coding strand is amplified with PCR primers #1680 and "B" and cloned into the vector as described above, A plasmid containing the desired sequence is isolated, and used for clotting multiple copies of the permuted sequence at the Ava I site. The multimeric gene is transferred to expression plasmid pTrc99a, and expressed after induction with IPTG. Inclusion bodies are purified by cycles of sonication and centrifugation. Partial cyanogen bromide cleavage of the multidomain protein gives a ladder of bands that are multimers of 10 kilodaltons.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A protein ladder comprising:
a collection of polypeptide fragments obtained by the partial cleavage of a polypeptide comprising multiple polypeptide repeats of identical sequence by one or more cleaving agents wherein;
(a) the protein ladder contains at least 3 polypeptide fragments of different size;
(b) the polypeptide comprising multiple polypeptide repeats comprises at least 3 repeats; and
(c) the size of each fragment in kilodaltons is an integral multiple of the size of the repeat.

2. The protein ladder according to claim 1, wherein the cleaving agent is cyanogen bromide.

3. The protein ladder according to claim 1, wherein the cleaving agent is a protease.

4. The protein ladder according to claim 1, wherein the polypeptide comprising multiple polypeptide repeats comprises at least 5 polypeptide repeats.

5. The protein ladder according to claim 1, wherein the polypeptide comprising multiple polypeptide repeats comprises at least 10 polypeptide repeats.

6. A polypeptide comprising a) multiple polypeptide repeats of identical sequence and b) sites for cleavage of said polypeptide into at least 3 polypeptide fragments, wherein the size of each fragment in kilodaltons is an integral multiple of the size of the repeat.

7. The polypeptide according to claim 6, wherein the cleaving site is methionine.

8. The polypeptide according to claim 6, wherein the cleaving site is a recognition site for a protease.

9. The polypeptide according to claim 6, wherein the polypeptide comprises at least 5 polypeptide repeats.

10. The polypeptide according to claim 6, wherein the polypeptide comprises at least 10 polypeptide repeats.

11. A protein marker kit comprising a carrier means having in close confinement therein at least one container means where the first container means contains the protein ladder according to claim 1.

12. A method of using a protein ladder to estimate the size of a sample protein comprising:
(a) electrophoresing simultaneously in separate lanes on a gel the protein ladder of claim 1 and the sample protein; and
(b) comparing the size of fragments of said protein ladder with the size of said ample protein.

* * * * *

SEQUENCE LISTING ( 1 ) GENERAL INFORMATION:

( i i i ) NUMBER OF SEQUENCES: 49

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( D ) TOPOLOGY: both ( x i ) SEQUENCE DESCRIPTION: SEQ ID NO:1:

Leu Val Pro Arg Gly Ser Pro
    1                 5

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: both ( x i ) SEQUENCE DESCRIPTION: SEQ ID NO:2:

Ile Glu Gly Arg
    1

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( D ) TOPOLOGY: both ( x i ) SEQUENCE DESCRIPTION: SEQ ID NO:3:

Pro Phe His Leu Leu Val Tyr
    1                 5

( 2 ) INFORMATION FOR SEQ ID NO:4:

( i ) SEQUENCE CHARACTERISTICS:
        ( A ) LENGTH: 88 amino acids
        ( B ) TYPE: amino acid
        ( D ) TOPOLOGY: both ( x i ) SEQUENCE DESCRIPTION: SEQ ID NO:4:

Met Gly Phe Ser Ser Glu Asp Lys Gly Glu Trp Lys Leu Lys Leu Asp
    1               5                 10                 15

Asn Ala Gly Asn Gly Gln Ala Val Ile Arg Phe Leu Pro Ser Lys Asn
                  20                 25                 30

Asp Glu Gln Ala Pro Phe Ala Ile Leu Val Asn His Gly Phe Lys Lys
             35                 40                 45

Asn Gly Lys Trp Tyr Ile Glu Thr Ser Ser Thr His Asp Tyr Asp Ser
        50                 55                 60

Pro Val Gln Tyr Ile Ser Lys Asn Asp Leu Gly Tyr Asn Thr Asp Asn
    65                 70                 75                 80

Lys Glu Tyr Val Leu Val Lys Leu
                  85

( 2 ) INFORMATION FOR SEQ ID NO:5:

( i ) SEQUENCE CHARACTERISTICS:
        ( A ) LENGTH: 528 amino acids
        ( B ) TYPE: amino acid (D) TOPOLOGY: both (xi) SEQUENCE DESCRIPTION: SEQ ID NO:5:

| Met 1 | Gly | Phe | Ser | Ser 5 | Glu | Asp | Lys | Gly | Glu 10 | Trp | Lys | Leu | Lys | Leu 15 | Asp |
|---|---|---|---|---|---|---|---|---|---|---|---|---|---|---|---|
| Asn | Ala | Gly | Asn 20 | Gly | Gln | Ala | Val | Ile 25 | Arg | Phe | Leu | Pro | Ser 30 | Lys | Asn |
| Asp | Glu | Gln 35 | Ala | Pro | Phe | Ala | Ile 40 | Leu | Val | Asn | His | Gly 45 | Phe | Lys | Lys |
| Asn | Gly 50 | Lys | Trp | Tyr | Ile | Glu 55 | Thr | Ser | Ser | Thr | His 60 | Asp | Tyr | Asp | Ser |
| Pro 65 | Val | Gln | Tyr | Ile | Ser 70 | Lys | Asn | Asp | Leu | Gly 75 | Tyr | Asn | Thr | Asp | Asn 80 |
| Lys | Glu | Tyr | Val | Leu 85 | Val | Lys | Leu | Met | Gly 90 | Phe | Ser | Ser | Glu | Asp 95 | Lys |
| Gly | Glu | Trp | Lys 100 | Leu | Lys | Leu | Asp | Asn 105 | Ala | Gly | Asn | Gly | Gln 110 | Ala | Val |
| Ile | Arg | Phe 115 | Leu | Pro | Ser | Lys | Asn 120 | Asp | Glu | Gln | Ala | Pro 125 | Phe | Ala | Ile |
| Leu | Val 130 | Asn | His | Gly | Phe | Lys 135 | Lys | Asn | Gly | Lys | Trp 140 | Tyr | Ile | Glu | Thr |
| Ser 145 | Ser | Thr | His | Asp | Tyr 150 | Asp | Ser | Pro | Val | Gln 155 | Tyr | Ile | Ser | Lys | Asn 160 |
| Asp | Leu | Gly | Tyr | Asn 165 | Thr | Asp | Asn | Lys | Glu 170 | Tyr | Val | Leu | Val | Lys 175 | Leu |
| Met | Gly | Phe | Ser 180 | Ser | Glu | Asp | Lys | Gly 185 | Glu | Trp | Lys | Leu | Lys 190 | Leu | Asp |
| Asn | Ala | Gly 195 | Asn | Gly | Gln | Ala | Val 200 | Ile | Arg | Phe | Leu | Pro 205 | Ser | Lys | Asn |
| Asp | Glu 210 | Gln | Ala | Pro | Phe | Ala 215 | Ile | Leu | Val | Asn | His 220 | Gly | Phe | Lys | Lys |
| Asn 225 | Gly | Lys | Trp | Tyr | Ile 230 | Glu | Thr | Ser | Ser | Thr 235 | His | Asp | Tyr | Asp | Ser 240 |
| Pro | Val | Gln | Tyr | Ile 245 | Ser | Lys | Asn | Asp | Leu 250 | Gly | Tyr | Asn | Thr | Asp 255 | Asn |
| Lys | Glu | Tyr | Val 260 | Leu | Val | Lys | Leu | Met 265 | Gly | Phe | Ser | Ser | Glu 270 | Asp | Lys |
| Gly | Glu | Trp 275 | Lys | Leu | Lys | Leu | Asp 280 | Asn | Ala | Gly | Asn | Gly 285 | Gln | Ala | Val |
| Ile | Arg 290 | Phe | Leu | Pro | Ser | Lys 295 | Asn | Asp | Glu | Gln | Ala 300 | Pro | Phe | Ala | Ile |
| Leu 305 | Val | Asn | His | Gly | Phe 310 | Lys | Lys | Asn | Gly | Lys 315 | Trp | Tyr | Ile | Glu | Thr 320 |
| Ser | Ser | Thr | His | Asp 325 | Tyr | Asp | Ser | Pro | Val 330 | Gln | Tyr | Ile | Ser | Lys 335 | Asn |
| Asp | Leu | Gly | Tyr 340 | Asn | Thr | Asp | Asn | Lys 345 | Glu | Tyr | Val | Leu | Val 350 | Lys | Leu |
| Met | Gly | Phe 355 | Ser | Ser | Glu | Asp | Lys 360 | Gly | Glu | Trp | Lys | Leu 365 | Lys | Leu | Asp |
| Asn | Ala 370 | Gly | Asn | Gly | Gln | Ala 375 | Val | Ile | Arg | Phe | Leu 380 | Pro | Ser | Lys | Asn |
| Asp 385 | Glu | Gln | Ala | Pro | Phe 390 | Ala | Ile | Leu | Val | Asn 395 | His | Gly | Phe | Lys | Lys 400 |
| Asn | Gly | Lys | Trp | Tyr 405 | Ile | Glu | Thr | Ser | Ser 410 | Thr | His | Asp | Tyr | Asp 415 | Ser |

```
        Pro   Val   Gln   Tyr   Ile   Ser   Lys   Asn   Asp   Leu   Gly   Tyr   Asn   Thr   Asp   Asn
                          420                           425                           430

Lys   Glu   Tyr   Val   Leu   Val   Lys   Leu   Met   Gly   Phe   Ser   Ser   Glu   Asp   Lys
                    435                           440                           445

Gly   Glu   Trp   Lys   Leu   Lys   Leu   Asp   Asn   Ala   Gly   Asn   Gly   Gln   Ala   Val
              450                           455                           460

Ile   Arg   Phe   Leu   Pro   Ser   Lys   Asn   Asp   Glu   Gln   Ala   Pro   Phe   Ala   Ile
        465                           470                           475                           480

Leu   Val   Asn   His   Gly   Phe   Lys   Lys   Asn   Gly   Lys   Trp   Tyr   Ile   Glu   Thr
                                485                           490                           495

Ser   Ser   Thr   His   Asp   Tyr   Asp   Ser   Pro   Val   Gln   Tyr   Ile   Ser   Lys   Asn
                          500                           505                           510

Asp   Leu   Gly   Tyr   Asn   Thr   Asp   Asn   Lys   Glu   Tyr   Val   Leu   Val   Lys   Leu
                    515                           520                           525
```

(2) INFORMATION FOR SEQ ID NO:6:

(i) SEQUENCE CHARACTERISTICS:
        (A) LENGTH: 6 amino acids
        (B) TYPE: amino acid
        (D) TOPOLOGY: both (xi) SEQUENCE DESCRIPTION: SEQ ID NO:6:

```
        His   His   His   His   His   His
        1                       5
```

(2) INFORMATION FOR SEQ ID NO:7:

(i) SEQUENCE CHARACTERISTICS:
        (A) LENGTH: 87 amino acids
        (B) TYPE: amino acid
        (D) TOPOLOGY: both (xi) SEQUENCE DESCRIPTION: SEQ ID NO:7:

```
        Met   Gly   Phe   Ser   Ser   Glu   Asp   Lys   Gly   Glu   Trp   Lys   Leu   Lys   Leu   Asp
        1                       5                           10                            15

Asn   Ala   Gly   Asn   Gly   Gln   Ala   Val   Ile   Arg   Phe   Leu   Pro   Ser   Lys   Asn
                          20                            25                            30

Asp   Glu   Gln   Ala   Pro   Phe   Ala   Ile   Leu   Val   Asn   His   Gly   Phe   Lys   Lys
                    35                            40                            45

Asn   Gly   Lys   Trp   Tyr   Ile   Glu   Thr   Ser   Ser   Thr   His   Asp   Tyr   Asp   Ser
              50                            55                            60

Pro   Val   Gln   Tyr   Ile   Ser   Lys   Asn   Asp   Leu   Gly   Tyr   Asn   Thr   Asp   Asn
        65                            70                            75                            80

Lys   His   His   His   His   His   His
                                85
```

(2) INFORMATION FOR SEQ ID NO:8:

(i) SEQUENCE CHARACTERISTICS:
        (A) LENGTH: 527 amino acids
        (B) TYPE: amino acid
        (D) TOPOLOGY: both (xi) SEQUENCE DESCRIPTION: SEQ ID NO:8:

```
        Met   Gly   Phe   Ser   Ser   Glu   Asp   Lys   Gly   Glu   Trp   Lys   Leu   Lys   Leu   Asp
        1                       5                           10                            15

Asn   Ala   Gly   Asn   Gly   Gln   Ala   Val   Ile   Arg   Phe   Leu   Pro   Ser   Lys   Asn
                          20                            25                            30

Asp   Glu   Gln   Ala   Pro   Phe   Ala   Ile   Leu   Val   Asn   His   Gly   Phe   Lys   Lys
                    35                            40                            45

Asn   Ala   Lys   Trp   Tyr   Ile   Glu   Thr   Ser   Ser   Thr   His   Asp   Tyr   Asp   Ser
```

|  | 50 |  |  |  |  | 55 |  |  |  | 60 |  |  |  |
|---|---|---|---|---|---|---|---|---|---|---|---|---|---|
| Pro | Val | Gln | Tyr | Ile | Ser | Lys | Asn | Asp | Leu | Gly | Tyr | Asn | Thr | Asp | Asn |
| 65 |  |  |  |  | 70 |  |  |  | 75 |  |  |  | 80 |
| Lys | Glu | Tyr | Val | Leu | Val | Lys | Leu | Met | Gly | Phe | Ser | Ser | Glu | Asp | Lys |
|  |  |  |  | 85 |  |  |  | 90 |  |  |  |  | 95 |
| Gly | Glu | Trp | Lys | Leu | Lys | Leu | Asp | Asn | Ala | Gly | Asn | Gly | Gln | Ala | Val |
|  |  |  | 100 |  |  |  | 105 |  |  |  | 110 |
| Ile | Arg | Phe | Leu | Pro | Ser | Lys | Asn | Asp | Glu | Gln | Ala | Pro | Phe | Ala | Ile |
|  |  | 115 |  |  |  | 120 |  |  |  | 125 |
| Leu | Val | Asn | His | Gly | Phe | Lys | Lys | Asn | Gly | Lys | Trp | Tyr | Ile | Glu | Thr |
| 130 |  |  |  | 135 |  |  |  | 140 |
| Ser | Ser | Thr | His | Asp | Tyr | Asp | Ser | Pro | Val | Gln | Tyr | Ile | Ser | Lys | Asn |
| 145 |  |  |  | 150 |  |  |  | 155 |  |  |  | 160 |
| Asp | Leu | Gly | Tyr | Asn | Thr | Asp | Asn | Lys | Glu | Tyr | Val | Leu | Val | Lys | Leu |
|  |  |  | 165 |  |  |  | 170 |  |  |  | 175 |
| Met | Gly | Phe | Ser | Ser | Glu | Asp | Lys | Gly | Glu | Trp | Lys | Leu | Lys | Leu | Asp |
|  |  |  | 180 |  |  |  | 185 |  |  |  | 190 |
| Asn | Ala | Gly | Asn | Gly | Gln | Ala | Val | Ile | Arg | Phe | Leu | Pro | Ser | Lys | Asn |
|  |  | 195 |  |  |  | 200 |  |  |  | 205 |
| Asp | Glu | Gln | Ala | Pro | Phe | Ala | Ile | Leu | Val | Asn | His | Gly | Phe | Lys | Lys |
| 210 |  |  |  | 215 |  |  |  | 220 |
| Asn | Gly | Lys | Trp | Tyr | Ile | Glu | Thr | Ser | Ser | Thr | His | Asp | Tyr | Asp | Ser |
| 225 |  |  |  | 230 |  |  |  | 235 |  |  |  | 240 |
| Pro | Val | Gln | Tyr | Ile | Ser | Lys | Asn | Asp | Leu | Gly | Tyr | Asn | Thr | Asp | Asn |
|  |  |  | 245 |  |  |  | 250 |  |  |  | 255 |
| Lys | Glu | Tyr | Val | Leu | Val | Lys | Leu | Met | Gly | Phe | Ser | Ser | Glu | Asp | Lys |
|  |  |  | 260 |  |  |  | 265 |  |  |  | 270 |
| Gly | Glu | Trp | Lys | Leu | Lys | Leu | Asp | Asn | Ala | Gly | Asn | Gly | Gln | Ala | Val |
|  |  |  | 275 |  |  |  | 280 |  |  |  | 285 |
| Ile | Arg | Phe | Leu | Pro | Ser | Lys | Asn | Asp | Glu | Gln | Ala | Pro | Phe | Ala | Ile |
|  |  | 290 |  |  |  | 295 |  |  |  | 300 |
| Leu | Val | Asn | His | Gly | Phe | Lys | Lys | Asn | Gly | Lys | Trp | Tyr | Ile | Glu | Thr |
| 305 |  |  |  | 310 |  |  |  | 315 |  |  |  | 320 |
| Ser | Ser | Thr | His | Asp | Tyr | Asp | Ser | Pro | Val | Gln | Tyr | Ile | Ser | Lys | Asn |
|  |  |  | 325 |  |  |  | 330 |  |  |  | 335 |
| Asp | Leu | Gly | Tyr | Asn | Thr | Asp | Asn | Lys | Glu | Tyr | Val | Leu | Val | Lys | Leu |
|  |  |  | 340 |  |  |  | 345 |  |  |  | 350 |
| Met | Gly | Phe | Ser | Ser | Glu | Asp | Lys | Gly | Glu | Trp | Lys | Leu | Lys | Leu | Asp |
|  |  |  | 355 |  |  |  | 360 |  |  |  | 365 |
| Asn | Ala | Gly | Asn | Gly | Gln | Ala | Val | Ile | Arg | Phe | Leu | Pro | Ser | Lys | Asn |
|  |  | 370 |  |  |  | 375 |  |  |  | 380 |
| Asp | Glu | Gln | Ala | Pro | Phe | Ala | Ile | Leu | Val | Asn | His | Gly | Phe | Lys | Lys |
| 385 |  |  |  | 390 |  |  |  | 395 |  |  |  | 400 |
| Asn | Gly | Lys | Trp | Tyr | Ile | Glu | Thr | Ser | Ser | Thr | His | Asp | Tyr | Asp | Ser |
|  |  |  | 405 |  |  |  | 410 |  |  |  | 415 |
| Pro | Val | Gln | Tyr | Ile | Ser | Lys | Asn | Asp | Leu | Gly | Tyr | Asn | Thr | Asp | Asn |
|  |  |  | 420 |  |  |  | 425 |  |  |  | 430 |
| Lys | Glu | Tyr | Val | Leu | Val | Lys | Leu | Met | Gly | Phe | Ser | Ser | Glu | Asp | Lys |
|  |  |  | 435 |  |  |  | 440 |  |  |  | 445 |
| Gly | Glu | Trp | Lys | Leu | Lys | Leu | Asp | Asn | Ala | Gly | Asn | Gly | Gln | Ala | Val |
|  |  |  | 450 |  |  |  | 455 |  |  |  | 460 |
| Ile | Arg | Phe | Leu | Pro | Ser | Lys | Asn | Asp | Glu | Gln | Ala | Pro | Phe | Ala | Ile |
| 465 |  |  |  | 470 |  |  |  | 475 |  |  |  | 480 |
| Leu | Val | Asn | His | Gly | Phe | Lys | Lys | Asn | Gly | Lys | Trp | Tyr | Ile | Glu | Thr |
|  |  |  | 485 |  |  |  | 490 |  |  |  | 495 |

| Ser | Ser | Thr | His | Asp | Tyr | Asp | Ser | Pro | Val | Gln | Tyr | Ile | Ser | Lys | Asn |
|-----|-----|-----|-----|-----|-----|-----|-----|-----|-----|-----|-----|-----|-----|-----|-----|
|     |     |     | 500 |     |     |     |     | 505 |     |     |     |     | 510 |     |     |

| Asp | Leu | Gly | Tyr | Asn | Thr | Asp | Asn | Lys | His | His | His | His | His |
|-----|-----|-----|-----|-----|-----|-----|-----|-----|-----|-----|-----|-----|-----|
|     |     |     | 515 |     |     |     | 520 |     |     |     |     | 525 |     |

( 2 ) INFORMATION FOR SEQ ID NO:9:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: both ( x i ) SEQUENCE DESCRIPTION: SEQ ID NO:9:

ATGGGTTTTT CTTCTGAAGA TAAAGGCGAG TGGAAACTGA AACTCGATAA TGCGGG      56

( 2 ) INFORMATION FOR SEQ ID NO:10:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: both ( x i ) SEQUENCE DESCRIPTION: SEQ ID NO:10:

TAACGGTCAA GCAGTAATTC GTTTCTTCC GTCTAAAAAT GATGAACAAG CACCA      55

( 2 ) INFORMATION FOR SEQ ID NO:11:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: both ( x i ) SEQUENCE DESCRIPTION: SEQ ID NO:11:

TTCGCAATTC TTGTAAATCA CGGTTTCAAG AAAAATGGTA AATGGTATAT TGAAA      55

( 2 ) INFORMATION FOR SEQ ID NO:12:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: both ( x i ) SEQUENCE DESCRIPTION: SEQ ID NO:12:

CATCATCTAC CCATGATTAC GATTCTCCAG TACAATACAT CAGTAAAAAT GAT      53

( 2 ) INFORMATION FOR SEQ ID NO:13:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: both ( x i ) SEQUENCE DESCRIPTION: SEQ ID NO:13:

CTCGGGTACA ACACTGACAA TAAAGAGTAC GTTCTTGTTA AACTT      45

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: both ( x i ) SEQUENCE DESCRIPTION: SEQ ID NO:14:

ACTGCTTGAC CGTTACCCGC ATTATCGAGT 30

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: both ( x i ) SEQUENCE DESCRIPTION: SEQ ID NO:15:

TACAAGAATT GCGAATGGTG CTTGTTCATC 30

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: both ( x i ) SEQUENCE DESCRIPTION: SEQ ID NO:16:

CATGGGTAGA TGATGTTTCA ATATACCATT 30

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: both ( x i ) SEQUENCE DESCRIPTION: SEQ ID NO:17:

AGTGTTGTAC CCGAGATCAT TTTTACTGAT 30

( 2 ) INFORMATION FOR SEQ ID NO:18:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: both ( x i ) SEQUENCE DESCRIPTION: SEQ ID NO:18:

AGAAGAAAAA CCCATAAGTT TAACAAGAAC 30

( 2 ) INFORMATION FOR SEQ ID NO:19:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: both ( x i ) SEQUENCE DESCRIPTION: SEQ ID NO:19:

GAUAUAUCCA UGGGTTTTTC TTCTGAAGAT AAAG 34

( 2 ) INFORMATION FOR SEQ ID NO:20:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: both ( x i ) SEQUENCE DESCRIPTION: SEQ ID NO:20:

GAUUACUUAU UAAAGTTTAA CAAGAACGTA CTCTT 35

( 2 ) INFORMATION FOR SEQ ID NO:21:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: both ( x i ) SEQUENCE DESCRIPTION: SEQ ID NO:21:

GAUAUAUCCA UGCTCGGGTA CAACACTGAC AA        32

( 2 ) INFORMATION FOR SEQ ID NO:22:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: both ( x i ) SEQUENCE DESCRIPTION: SEQ ID NO:22:

GAUUACUUAU UACCCGAGAT CATTTTACT GATGTATTGT AC        42

( 2 ) INFORMATION FOR SEQ ID NO:23:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: both ( x i ) SEQUENCE DESCRIPTION: SEQ ID NO:23:

AGCTAGAAAT AATTTGTTT AACTTAAGA AGGAGATATA TCCATG        46

( 2 ) INFORMATION FOR SEQ ID NO:24:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: both ( x i ) SEQUENCE DESCRIPTION: SEQ ID NO:24:

TCCTTCTTAA AGTTAAACAA AATTATTTCT        30

( 2 ) INFORMATION FOR SEQ ID NO:25:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: both ( x i ) SEQUENCE DESCRIPTION: SEQ ID NO:25:

AATTCCAGGT CGACTCTAGA GATTACTTAT TA        32

( 2 ) INFORMATION FOR SEQ ID NO:26:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: both ( x i ) SEQUENCE DESCRIPTION: SEQ ID NO:26:

TCTAGAGTCG ACCTGG        16

( 2 ) INFORMATION FOR SEQ ID NO:27:

( i ) SEQUENCE CHARACTERISTICS:
        ( A ) LENGTH: 792 base pairs (B) TYPE: nucleic acid
(C) STRANDEDNESS: single
(D) TOPOLOGY: both (xi) SEQUENCE DESCRIPTION: SEQ ID NO:27:

| | | | | | |
|---|---|---|---|---|---|
| ATGGGTTTTT | CTTCTGAAGA | TAAAGGCGAG | TGGAAACTGA | AACTCGATAA | TGCGGGTAAC | 60 |
| GGTCAAGCAG | TAATTCGTTT | TCTTCCGTCT | AAAAATGATG | AACAAGCCCC | ATTCGCAATT | 120 |
| CTTGTAAATC | ACGGTTTCAA | GAAAATGGT | AAATGGTATA | TTGAAACATC | ATCTACCCAT | 180 |
| GATTACGATT | CTCCAGTACA | ATACATCAGT | AAAAATGATC | TCGGGTACAA | CACTGACAAT | 240 |
| AAAGAGTACG | TTCTTGTTAA | ACTTATGGGT | TTTTCTTCTG | AAGATAAAGG | CGAGTGGAAA | 300 |
| CTGAAACTCG | ATAATGCGGG | TAACGGTCAA | GCAGTAATTC | GTTTCTTCC | GTCTAAAAAT | 360 |
| GATGAACAAG | CACCATTCGC | AATTCTTGTA | AATCACGGTT | TCAAGAAAAA | TGGTAAATGG | 420 |
| TATATTGAAA | CATCATCTAC | CCATGATTAC | GATTCTCCAG | TACAATACAT | CAGTAAAAAT | 480 |
| GATCTCGGGT | ACAACACTGA | CAATAAAGAG | TACGTTCTTG | TTAAACTTAT | GGGTTTTCT | 540 |
| TCTGAAGATA | AAGGCGAGTG | GAAACTGAAA | CTCGATAATG | CGGGTAACGG | TCAAGCAGTA | 600 |
| ATTCGTTTTC | TTCCGTCTAA | AAATGATGAA | CAAGCACCAT | TCGCAATTCT | TGTAAATCAC | 660 |
| GGTTTCAAGA | AAAATGGTAA | ATGGTATATT | GAAACATCAT | CTACCCATGA | TTACGATTCT | 720 |
| CCAGTACAAT | ACATCAGTAA | AAATGATCTC | GGGTACAACA | CTGACAATAA | AGAGTACGTT | 780 |
| CTTGTTAAAC | TT | | | | | 792 |

(2) INFORMATION FOR SEQ ID NO:28:

(i) SEQUENCE CHARACTERISTICS:
(A) LENGTH: 264 amino acids
(B) TYPE: amino acid
(C) STRANDEDNESS: single
(D) TOPOLOGY: both (xi) SEQUENCE DESCRIPTION: SEQ ID NO:28:

```
Met Gly Phe Ser Ser Glu Asp Lys Gly Glu Trp Lys Leu Lys Leu Asp
 1               5                  10                  15

Asn Ala Gly Asn Gly Gln Ala Val Ile Arg Phe Leu Pro Ser Lys Asn
            20                  25                  30

Asp Glu Gln Ala Pro Phe Ala Ile Leu Val Asn His Gly Phe Lys Lys
        35                  40                  45

Asn Gly Lys Trp Tyr Ile Glu Thr Ser Ser Thr His Asp Tyr Asp Ser
    50                  55                  60

Pro Val Gln Tyr Ile Ser Lys Asn Asp Leu Gly Tyr Asn Thr Asp Asn
65                  70                  75                  80

Lys Glu Tyr Val Leu Val Lys Leu Met Gly Phe Ser Ser Glu Asp Lys
                85                  90                  95

Gly Glu Trp Lys Leu Lys Leu Asp Asn Ala Gly Asn Gly Gln Ala Val
            100                 105                 110

Ile Arg Phe Leu Pro Ser Lys Asn Asp Glu Gln Ala Pro Phe Ala Ile
        115                 120                 125

Leu Val Asn His Gly Phe Lys Lys Asn Gly Lys Trp Tyr Ile Glu Thr
    130                 135                 140

Ser Ser Thr His Asp Tyr Asp Ser Pro Val Gln Tyr Ile Ser Lys Asn
145                 150                 155                 160

Asp Leu Gly Tyr Asn Thr Asp Asn Lys Glu Tyr Val Leu Val Lys Leu
                165                 170                 175

Met Gly Phe Ser Ser Glu Asp Lys Gly Glu Trp Lys Leu Lys Leu Asp
            180                 185                 190

Asn Ala Gly Asn Gly Gln Ala Val Ile Arg Phe Leu Pro Ser Lys Asn
```

|                | 195                |                  | 200               |                  | 205                |          |
|---|---|---|---|---|---|---|

Asp Glu Gln Ala Pro Phe Ala Ile Leu Val Asn His Gly Phe Lys Lys
   210                215                220

Asn Gly Lys Trp Tyr Ile Glu Thr Ser Ser Thr His Asp Tyr Asp Ser
225                230                235                240

Pro Val Gln Tyr Ile Ser Lys Asn Asp Leu Gly Tyr Asn Thr Asp Asn
              245                250                255

Lys Glu Tyr Val Leu Val Lys Leu
            260

( 2 ) INFORMATION FOR SEQ ID NO:29:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: both ( x i ) SEQUENCE DESCRIPTION: SEQ ID NO:29:

| CTCGGGTACA | ACACTGACAA | TAAACACCAC | CACCACCACC | AC | 42 |
|---|---|---|---|---|---|

( 2 ) INFORMATION FOR SEQ ID NO:30:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: both ( x i ) SEQUENCE DESCRIPTION: SEQ ID NO:30:

| GAUUACUUAU | UAGTGGTGGT | GGTGGTGGTG | TTT | 33 |
|---|---|---|---|---|

( 2 ) INFORMATION FOR SEQ ID NO:31:

( i ) SEQUENCE CHARACTERISTICS:
        ( A ) LENGTH: 789 base pairs
        ( B ) TYPE: nucleic acid
        ( C ) STRANDEDNESS: single
        ( D ) TOPOLOGY: both ( x i ) SEQUENCE DESCRIPTION: SEQ ID NO:31:

| ATGGGTTTTT | CTTCTGAAGA | TAAAGGCGAG | TGGAAACTGA | AACTCGATAA | TGCGGGTAAC | 60 |
|---|---|---|---|---|---|---|
| GGTCAAGCAG | TAATTCGTTT | TCTTCCGTCT | AAAAATGATG | AACAAGCACC | ATTCGCAATT | 120 |
| CTTGTAAATC | ACGGTTTCAA | GAAAAATGCT | AAATGGTATA | TTGAAACATC | ATCTACCCAT | 180 |
| GATTACGATT | CTCCAGTACA | ATACATCAGT | AAAAATGATC | TCGGGTACAA | CACTGACAAT | 240 |
| AAAGAGTACG | TTCTTGTTAA | ACTTATGGGT | TTTTCTTCTG | AAGATAAAGG | CGAGTGGAAA | 300 |
| CTGAAACTCG | ATAATGCGGG | TAACGGTCAA | GCAGTAATTC | GTTTTCTTCC | GTCTAAAAAT | 360 |
| GATGAACAAG | CCCCATTCGC | AATTCTTGTA | AATCACGGTT | TCAAGAAAAA | TGGTAAATGG | 420 |
| TATATTGAAA | CATCATCTAC | CCATGATTAC | GATTCTCCAG | TACAATACAT | CAGTAAAAAT | 480 |
| GATCTCGGGT | ACAACACTGA | CAATAAAGAG | TACGTTCTTG | TTAAACTTAT | GGGTTTTTCT | 540 |
| TCTGAAGATA | AAGGCGAGTG | GAAACTGAAA | CTCGATAATG | CGGGTAACGG | TCAAGCAGTA | 600 |
| ATTCGTTTTC | TTCCGTCTAA | AAATGATGAA | CAAGCCCCAT | TCGCAATTCT | TGTAAATCAC | 660 |
| GGTTTCAAGA | AAAATGGTAA | ATGGTATATT | GAAACATCAT | CTACCCATGA | TTACGATTCT | 720 |
| CCAGTACAAT | ACATCAGTAA | AAATGATCTC | GGGTACAACA | CTGACAATAA | ACACCACCAC | 780 |
| CACCACCAC  |            |            |            |            |            | 789 |

( 2 ) INFORMATION FOR SEQ ID NO:32:

( i ) SEQUENCE CHARACTERISTICS:
  ( A ) LENGTH: 263 amino acids
  ( B ) TYPE: amino acid
  ( D ) TOPOLOGY: both ( x i ) SEQUENCE DESCRIPTION: SEQ ID NO:32:

```
Met Gly Phe Ser Ser Glu Asp Lys Gly Glu Trp Lys Leu Lys Leu Asp
 1               5                  10                  15
Asn Ala Gly Asn Gly Gln Ala Val Ile Arg Phe Leu Pro Ser Lys Asn
            20                  25                  30
Asp Glu Gln Ala Pro Phe Ala Ile Leu Val Asn His Gly Phe Lys Lys
        35                  40                  45
Asn Ala Lys Trp Tyr Ile Glu Thr Ser Ser Thr His Asp Tyr Asp Ser
50                  55                  60
Pro Val Gln Tyr Ile Ser Lys Asn Asp Leu Gly Tyr Asn Thr Asp Asn
65                  70                  75                  80
Lys Glu Tyr Val Leu Val Lys Leu Met Gly Phe Ser Ser Glu Asp Lys
                85                  90                  95
Gly Glu Trp Lys Leu Lys Leu Asp Asn Ala Gly Asn Gly Gln Ala Val
            100                 105                 110
Ile Arg Phe Leu Pro Ser Lys Asn Asp Glu Gln Ala Pro Phe Ala Ile
        115                 120                 125
Leu Val Asn His Gly Phe Lys Lys Asn Gly Lys Trp Tyr Ile Glu Thr
    130                 135                 140
Ser Ser Thr His Asp Tyr Asp Ser Pro Val Gln Tyr Ile Ser Lys Asn
145                 150                 155                 160
Asp Leu Gly Tyr Asn Thr Asp Asn Lys Glu Tyr Val Leu Val Lys Leu
                165                 170                 175
Met Gly Phe Ser Ser Glu Asp Lys Gly Glu Trp Lys Leu Lys Leu Asp
            180                 185                 190
Asn Ala Gly Asn Gly Gln Ala Val Ile Arg Phe Leu Pro Ser Lys Asn
        195                 200                 205
Asp Glu Gln Ala Pro Phe Ala Ile Leu Val Asn His Gly Phe Lys Lys
    210                 215                 220
Asn Gly Lys Trp Tyr Ile Glu Thr Ser Ser Thr His Asp Tyr Asp Ser
225                 230                 235                 240
Pro Val Gln Tyr Ile Ser Lys Asn Asp Leu Gly Tyr Asn Thr Asp Asn
                245                 250                 255
Lys His His His His His His
            260
```

( 2 ) INFORMATION FOR SEQ ID NO:33:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: both ( x i ) SEQUENCE DESCRIPTION: SEQ ID NO:33:

ATGGCTCACC ACCACCACCA CCACCCGCAC GTTAAAGTTG GTAAC    45

( 2 ) INFORMATION FOR SEQ ID NO:34:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: both ( x i ) SEQUENCE DESCRIPTION: SEQ ID NO:34:

CTGCACATCT TCGGTCGTCA CGGCGAAGGT TACAGCGG                                    38

( 2 ) INFORMATION FOR SEQ ID NO:35:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: both ( x i ) SEQUENCE DESCRIPTION: SEQ ID NO:35:

CCCGAGCTAC ACCGACGCTA ACCACAAACA CCTGAACTGG GACGAAAACA ACAAAAGCG            59

( 2 ) INFORMATION FOR SEQ ID NO:36:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: both ( x i ) SEQUENCE DESCRIPTION: SEQ ID NO:36:

AATACCTGAC CAACCCGAAA TACAAAATTC CGGGCAAAAC CAAAGGTAAA GCTTTCGGT            59

( 2 ) INFORMATION FOR SEQ ID NO:37:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: both ( x i ) SEQUENCE DESCRIPTION: SEQ ID NO:37:

GGCAAACTGA AGAAGACAA ACGTAACGAC CTGATCACCT ACCTGAAAGC TAAATGCGAA            60

( 2 ) INFORMATION FOR SEQ ID NO:38:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: both ( x i ) SEQUENCE DESCRIPTION: SEQ ID NO:38:

ACCGAAGATG TGCAGGTTAC CAACTTTAAC                                            30

( 2 ) INFORMATION FOR SEQ ID NO:39:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: both ( x i ) SEQUENCE DESCRIPTION: SEQ ID NO:39:

TCGGTGTAGC TCGGGCCGCT GTAACCTTCG                                            30

( 2 ) INFORMATION FOR SEQ ID NO:40:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: both ( x i ) SEQUENCE DESCRIPTION: SEQ ID NO:40:

GGTTGGTCAG GTATTCGCTT TTGTTGTTTT                                            30

( 2 ) INFORMATION FOR SEQ ID NO:41:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: both ( x i ) SEQUENCE DESCRIPTION: SEQ ID NO:41:

TTCTTTCAGT TTGCCACCGA AAGCTTTACC     30

( 2 ) INFORMATION FOR SEQ ID NO:42:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: both ( x i ) SEQUENCE DESCRIPTION: SEQ ID NO:42:

GAUAUAUCCA UGGCTCACCA CCACCAC     27

( 2 ) INFORMATION FOR SEQ ID NO:43:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: both ( x i ) SEQUENCE DESCRIPTION: SEQ ID NO:43:

GAUUACUUAU UAUUCGCATT TAGCTTTCAG GTA     33

( 2 ) INFORMATION FOR SEQ ID NO:44:

( i ) SEQUENCE CHARACTERISTICS:
        ( A ) LENGTH: 783 base pairs
        ( B ) TYPE: nucleic acid
        ( C ) STRANDEDNESS: single
        ( D ) TOPOLOGY: both ( x i ) SEQUENCE DESCRIPTION: SEQ ID NO:44:

| | | | | | | |
|---|---|---|---|---|---|---|
| ATGGCTCACC | ACCACCACCA | CCACCCGCAC | GTTAAAGTTG | GTAACCTGCA | CATCTTCGGT | 60 |
| CGTCACGGCG | AAGGTTACAG | CGGCCCGAGC | TACACCGACG | CTAACCACAA | ACACCTGAAC | 120 |
| TGGGACGAAA | ACAACAAAAG | CGAATACCTG | ACCAACCCGA | AATACAAAAT | TCCGGGCAAA | 180 |
| ACCAAGGTA | AAGCTTTCGG | TGGCAAACTG | AAAGAAGACA | AACGTAACGA | CCTGATCACC | 240 |
| TACCTGAAAG | CTAATGCGA | AATGGCTCAC | CACCACCACC | ACCACCCGCA | CGTTAAAGTT | 300 |
| GGTAACCTGC | ACATCTTCGG | TCGTCACGGC | GAAGGTTACA | GCGGCCCGAG | CTACACCGAC | 360 |
| GCTAACCACA | AACACCTGAA | CTGGGACGAA | AACAACAAAA | GCGAATACCT | GACCAACCCG | 420 |
| AAATACAAAA | TTCCGGGCAA | AACCAAGGT | AAAGCTTTCG | GTGGCAAACT | GAAAGAAGAC | 480 |
| AAACGTAACG | ACCTGATCAC | CTACCTGAAA | GCTAATGCG | AAATGGCTCA | CCACCACCAC | 540 |
| CACCACCCGC | ACGTTAAAGT | TGGTAACCTG | CACATCTTCG | GTCGTCACGG | CGAAGGTTAC | 600 |
| AGCGGCCCGA | GCTACACCGA | CGCTAACCAC | AAACACCTGA | ACTGGGACGA | AAACAACAAA | 660 |
| AGCGAATACC | TGACCAACCC | GAAATACAAA | ATTCCGGGCA | AAACCAAGG | TAAAGCTTTC | 720 |
| GGTGGCAAAC | TGAAAGAAGA | CAAACGTAAC | GACCTGATCA | CCTACCTGAA | AGCTAATGC | 780 |
| GAA | | | | | | 783 |

( 2 ) INFORMATION FOR SEQ ID NO:45:

( i ) SEQUENCE CHARACTERISTICS:
        ( A ) LENGTH: 261 amino acids
        ( B ) TYPE: amino acid ( C ) STRANDEDNESS: single
( D ) TOPOLOGY: both ( x i ) SEQUENCE DESCRIPTION: SEQ ID NO:45:

| Met | Ala | His | His | His | His | His | Pro | His | Val | Lys | Val | Gly | Asn | Leu |
|---|---|---|---|---|---|---|---|---|---|---|---|---|---|---|
| 1 | | | | 5 | | | | | 10 | | | | | 15 |

| His | Ile | Phe | Gly | Arg | His | Gly | Glu | Gly | Tyr | Ser | Gly | Pro | Ser | Tyr | Thr |
|---|---|---|---|---|---|---|---|---|---|---|---|---|---|---|---|
| | | | 20 | | | | 25 | | | | | 30 | | | |

| Asp | Ala | Asn | His | Lys | His | Leu | Asn | Trp | Asp | Glu | Asn | Asn | Lys | Ser | Glu |
|---|---|---|---|---|---|---|---|---|---|---|---|---|---|---|---|
| | | 35 | | | | | 40 | | | | | 45 | | | |

| Tyr | Leu | Thr | Asn | Pro | Lys | Tyr | Lys | Ile | Pro | Gly | Lys | Thr | Lys | Gly | Lys |
|---|---|---|---|---|---|---|---|---|---|---|---|---|---|---|---|
| | 50 | | | | 55 | | | | | 60 | | | | | |

| Ala | Phe | Gly | Gly | Lys | Leu | Lys | Glu | Asp | Lys | Arg | Asn | Asp | Leu | Ile | Thr |
|---|---|---|---|---|---|---|---|---|---|---|---|---|---|---|---|
| 65 | | | | 70 | | | | | 75 | | | | | 80 | |

| Tyr | Leu | Lys | Ala | Lys | Cys | Glu | Met | Ala | His | His | His | His | His | Pro |
|---|---|---|---|---|---|---|---|---|---|---|---|---|---|---|
| | | | 85 | | | | | 90 | | | | | 95 | |

| His | Val | Lys | Val | Gly | Asn | Leu | His | Ile | Phe | Gly | Arg | His | Gly | Glu | Gly |
|---|---|---|---|---|---|---|---|---|---|---|---|---|---|---|---|
| | | | 100 | | | | | 105 | | | | | 110 | | |

| Tyr | Ser | Gly | Pro | Ser | Tyr | Thr | Asp | Ala | Asn | His | Lys | His | Leu | Asn | Trp |
|---|---|---|---|---|---|---|---|---|---|---|---|---|---|---|---|
| | | 115 | | | | | 120 | | | | | 125 | | | |

| Asp | Glu | Asn | Asn | Lys | Ser | Glu | Tyr | Leu | Thr | Asn | Pro | Lys | Tyr | Lys | Ile |
|---|---|---|---|---|---|---|---|---|---|---|---|---|---|---|---|
| | 130 | | | | | 135 | | | | | 140 | | | | |

| Pro | Gly | Lys | Thr | Lys | Gly | Lys | Ala | Phe | Gly | Gly | Lys | Leu | Lys | Glu | Asp |
|---|---|---|---|---|---|---|---|---|---|---|---|---|---|---|---|
| 145 | | | | | 150 | | | | | 155 | | | | | 160 |

| Lys | Arg | Asn | Asp | Leu | Ile | Thr | Tyr | Leu | Lys | Ala | Lys | Cys | Glu | Met | Ala |
|---|---|---|---|---|---|---|---|---|---|---|---|---|---|---|---|
| | | | 165 | | | | | 170 | | | | | 175 | | |

| His | His | His | His | His | His | Pro | His | Val | Lys | Val | Gly | Asn | Leu | His | Ile |
|---|---|---|---|---|---|---|---|---|---|---|---|---|---|---|---|
| | | | 180 | | | | | 185 | | | | | 190 | | |

| Phe | Gly | Arg | His | Gly | Glu | Gly | Tyr | Ser | Gly | Pro | Ser | Tyr | Thr | Asp | Ala |
|---|---|---|---|---|---|---|---|---|---|---|---|---|---|---|---|
| | | 195 | | | | | 200 | | | | | 205 | | | |

| Asn | His | Lys | His | Leu | Asn | Trp | Asp | Glu | Asn | Asn | Lys | Ser | Glu | Tyr | Leu |
|---|---|---|---|---|---|---|---|---|---|---|---|---|---|---|---|
| | 210 | | | | | 215 | | | | | 220 | | | | |

| Thr | Asn | Pro | Lys | Tyr | Lys | Ile | Pro | Gly | Lys | Thr | Lys | Gly | Lys | Ala | Phe |
|---|---|---|---|---|---|---|---|---|---|---|---|---|---|---|---|
| 225 | | | | | 230 | | | | | 235 | | | | | 240 |

| Gly | Gly | Lys | Leu | Lys | Glu | Asp | Lys | Arg | Asn | Asp | Leu | Ile | Thr | Tyr | Leu |
|---|---|---|---|---|---|---|---|---|---|---|---|---|---|---|---|
| | | | | 245 | | | | | 250 | | | | | 255 | |

| Lys | Ala | Lys | Cys | Glu |
|---|---|---|---|---|
| | | | | 260 |

( 2 ) INFORMATION FOR SEQ ID NO:46:

( i ) SEQUENCE CHARACTERISTICS:
( A ) LENGTH: 48 base pairs
( B ) TYPE: nucleic acid
( C ) STRANDEDNESS: single
( D ) TOPOLOGY: both ( x i ) SEQUENCE DESCRIPTION: SEQ ID NO:46:

CTCGGGTACA ACACTGACAA TAAAGAGTCA GTTCTTGTTA AACTTATG. 48

( 2 ) INFORMATION FOR SEQ ID NO:47:

( i ) SEQUENCE CHARACTERISTICS:
( A ) LENGTH: 38 base pairs
( B ) TYPE: nucleic acid
( C ) STRANDEDNESS: single
( D ) TOPOLOGY: both ( x i ) SEQUENCE DESCRIPTION: SEQ ID NO:47:

GAUUACUUAU UACATAAGTT TAACAAGAAC GTACTCTT 38

(2) INFORMATION FOR SEQ ID NO:48:

(i) SEQUENCE CHARACTERISTICS:
        (A) LENGTH: 5 amino acids
        (B) TYPE: amino acid
        (C) STRANDEDNESS: single
        (D) TOPOLOGY: both (xi) SEQUENCE DESCRIPTION: SEQ ID NO:48:

```
Pro  Xaa  Xaa  Xaa  Gly
1                   5
```

(2) INFORMATION FOR SEQ ID NO:49:

(i) SEQUENCE CHARACTERISTICS:
        (A) LENGTH: 24 base pairs
        (B) TYPE: nucleic acid
        (C) STRANDEDNESS: single
        (D) TOPOLOGY: both (xi) SEQUENCE DESCRIPTION: SEQ ID NO:49:

ATGGCTCACC ACCACCACCA CCAC    24